Figure 1:
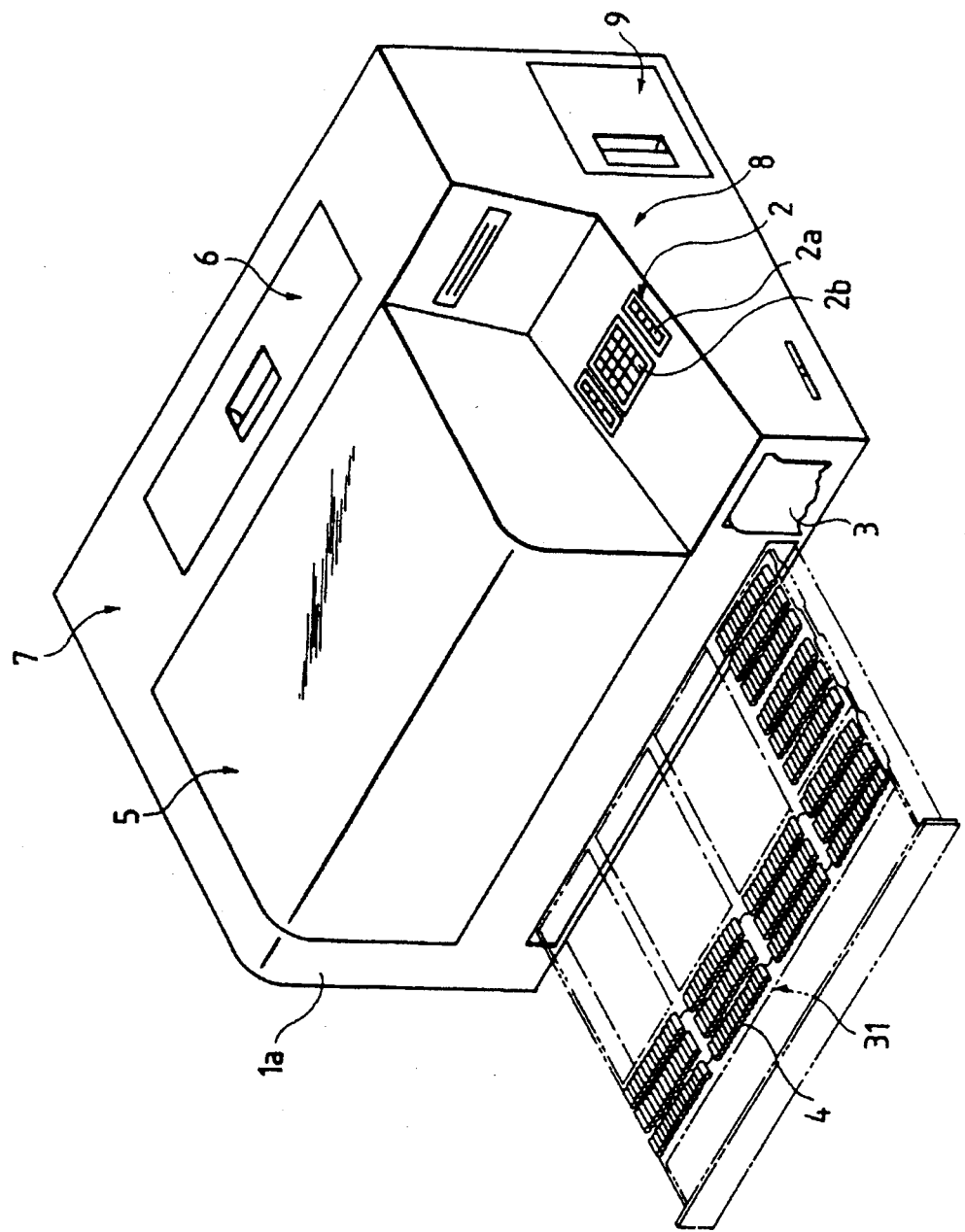
Figure 1A:
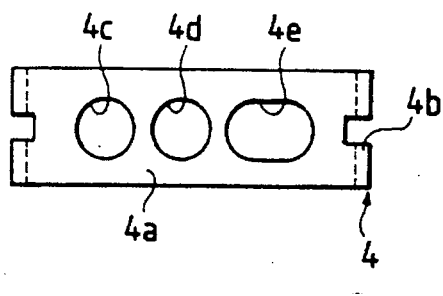

United States Patent [19]
Ashihara et al.

[11] Patent Number: 5,482,839
[45] Date of Patent: Jan. 9, 1996

[54] AUTOMATIC IMMUNOLOGICAL MEASURING SYSTEM

[76] Inventors: Yoshihiro Ashihara, 28-1, Fuchudanchi 2-402, Harumicho 1-chrome, Fuchu-shi, Tokyo 183, Japan; Isao Nishizono, 7-2, Higashinakagamidanchi 2-215, Tamagawacho 1-chome, Akishima-shi, Tokyo 196, Japan; Hidetaka Minakawa, 9-7-202, Hashimoto 4-chome, Sagamihara-shi, Kanagawa 229, Japan; Masahisa Okada, 11-1, Minaminaruse 3-chome, Machida-shi, Tokyo 194, Japan; Yasusuke Sakurabayashi, Green Hill Terada 129-206, Teradacho 432, Hachioji-shi, Tokyo 193, Japan; Fumio Watanabe, 3-16-10, Nanyodai, Hachioji-shi, Tokyo 192, Japan; Shin-ichi Wakana, 9-5, Nishisunacho 3-chome, Tachikawa-shi, Tokyo 190, Japan

[21] Appl. No.: 57,503

[22] Filed: May 4, 1993

Related U.S. Application Data

[62] Division of Ser. No. 915,124, Jul. 17, 1992, Pat. No. 5,290,708, which is a division of Ser. No. 677,686, Mar. 29, 1991, Pat. No. 5,158,895.

[30] Foreign Application Priority Data

| Mar. 30, 1990 | [JP] | Japan | 2-80993 |
| May 9, 1990 | [JP] | Japan | 2-119010 |
| Jun. 27, 1990 | [JP] | Japan | 2-166756 |
| Sep. 3, 1990 | [JP] | Japan | 2-91567 |

[51] Int. Cl.⁶ ............................... G01N 33/553
[52] U.S. Cl. .................. 435/7.9; 356/244; 356/246; 422/58; 422/63; 422/64; 422/102; 435/7.92; 435/287.2; 435/287.3; 436/47; 436/525; 436/526; 436/809
[58] Field of Search ................... 356/244, 246; 422/58, 63, 64, 65, 102; 435/7.9, 7.92, 291; 436/45–47, 525, 526, 809

[56] References Cited

U.S. PATENT DOCUMENTS

| 4,849,177 | 7/1989 | Jordan | 436/809 |
| 4,933,147 | 6/1990 | Hollar et al. | 422/64 |
| 4,956,148 | 9/1990 | Grandone | 422/63 |
| 4,970,053 | 11/1990 | Fechtner | 436/45 |
| 5,035,861 | 7/1991 | Grandone | 422/64 |
| 5,104,808 | 4/1992 | Lasha et al. | 422/64 |
| 5,167,922 | 12/1992 | Long | 422/58 |

*Primary Examiner*—Toni R. Scheiner
*Assistant Examiner*—Christopher L. Chin

[57] ABSTRACT

An automatic immunoassay apparatus utilizes cartridges each having at least two wells, a first well of said wells containing solid phase material carrying antigen or antibody, a second well of said wells containing antibody or antigen labelled with labelling compound. The wells may be sealed with a suitable sealing film before use and the sealing film is broken when the cartridge is to be used. The cartridges are transported to a predetermined position on a steppingly movable reaction line and conveyed thereby at a predetermined interval. While the reaction line steps, a sample, labelled antigen or antibody contained in the second well and substrate, if necessary, are added to the first well and stirred at predetermined timings and reaction between the sample and a reactive solution is measured under control of a control device having memory means storing operator selectable programs for various measuring methods.

6 Claims, 21 Drawing Sheets

TABLE 1-continued

| | Measurement of HTLV-I antibody | |
|---|---|---|
| Sample | | Count Number (x10³) (counts/5 sec) |
| negative serum | 4 | 0.005 |
| | 5 | 0.008 |
| | 1 | 0.042 |
| | 2 | 0.059 |
| | 3 | 0.054 |
| positive serum | 4 | 0.063 |
| | 1 | 0.599 |
| | 2 | 0.535 |
| | 3 | 0.542 |

VII—Measurement of CA19-9

1—Preparation of CA19-9 antibody bound particles

In a similar manner to II, anti CA 19-9 MCA sensitized ferrite particles were prepared by reacting 2 mg of anti CA19-9 monoclonal antibody (MCA) and washing it sufficiently (0.004% particle/2% BSA, 0.1M Tris-HCl, 1 mM $MgCl_2$, 0.1 mM $ZnCl_2$, pH 7.5).

2—Preparation of cartridge for particle type CA19-9 measurement

Figure 1D:
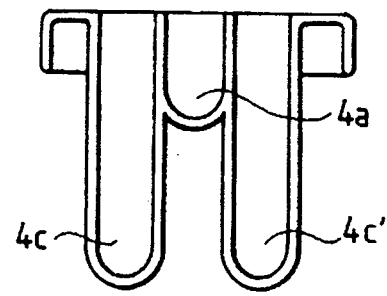
Figure 1B:
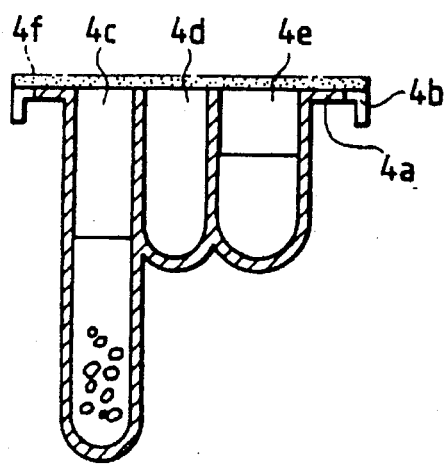
Figure 1E:
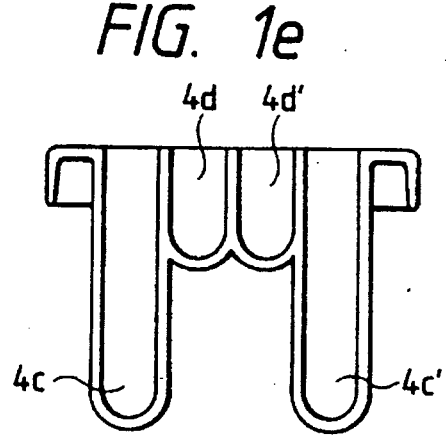
Figure 1C:
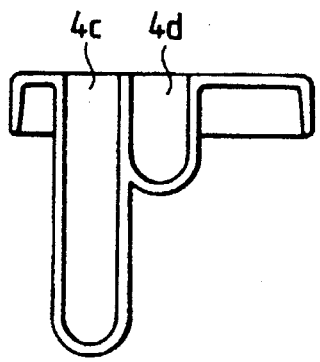
Figure 1F:
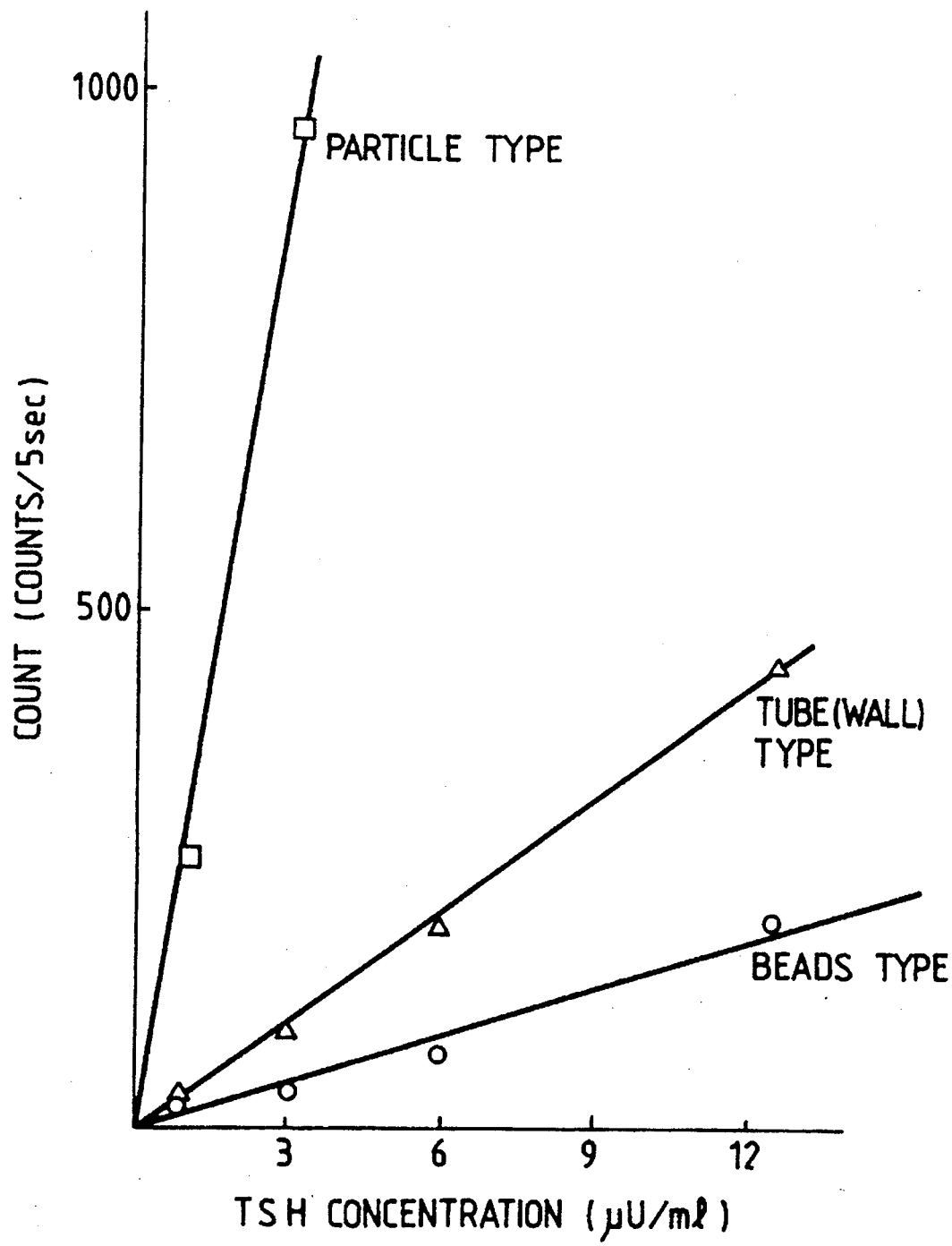

250 µl of anti CA19-9 mouse IgG sensitized ferrite particles were added to the well 4c of the cartridge 4 in FIG. 1c and 350 µl of alkali phosphatase sensitized anti CA19-9 mouse IgG-Fab solution (0.5 µg/ml) was added to the well 4d. The cartridge was heat sealed by a PET laminated aluminum foil.

3—Measurement of CA19-9

The aluminum seal used in VII-2 was preliminarily broken by the seal breaker and 20 µl of serum was added to the well 4c and after being stirred put as it is for 10 minutes. Then, The well 4c was faced to a permanent magnet whose surface magnetic field is 3000 Gauss to attract the particles. Supernatant was removed by decantation and,then, 0.2% physiological salt solution was added and stirred. Ferrite particles were attracted by the same magnet and supernatant was removed in a similar manner. This processing was repeated by 2 times. Then, 250 µl of the labelled antibody solution in the well 4d was added to the well 4c and stirred. After 10 minutes at room temperature, the ferrite particles were attracted and supernatant was removed. The processing was repeated 4 times. Then, 300 µl of same substrate solution used in IV was added and stirred. After 5 minutes at room temperature, luminance for 5 seconds was measured by the luminometer. The result is shown in Table 2.

Table 2

| | CA19-9 Measurement | |
|---|---|---|
| Serum Sample | Count Number (x10³) (counts/5 sec) | Amount of CA19-9 (µU/ml) |
| 1 | 0.208 | 1.9 |
| 2 | 1.408 | 19.3 |
| 3 | 4.560 | 59.5 |
| 4 | 2.144 | 31.6 |
| 5 | 8.575 | 108.9 |

VIII—Preparation of cartridge for particle type CA19-9 measurement

250 µl of anti CA19-9 mouse IgG sensitized ferrite particles prepared in VII-1 were added to the wells 4c and 4c' of the cartridge 4 in FIG. 1d and 350 µl of alkaliphosphatase sensitized anti CA19-9 mouse IgG-Fab solution (0.5 µg.ml) were added to the well 4e. These wells were heat sealed by a PET laminated aluminum foil.

1—Measurement of CA19-9

The aluminum seal used in VIII was preliminarily broken by the seal breaker and each 20 µl of different serums were added to the wells 4c and 4c', respectively, and after being stirred put as they are for 10 minutes. Then, The wells were faced to a permanent magnet whose surface magnetic field is 3000 Gauss to attract the particles. Supernatant was removed by decantation and,then, 0.2% physiological salt solution was added and stirred. Ferrite particles were attracted by the same magnet and supernatant was removed in the similar manner. This processing was repeated 2 times. Then, 250 µl of the labelled antibody solution in the well 4d was added to the wells 4c and 4c' and stirred. After 10 minutes at room temperature, the ferrite particles were attracted and supernatant was removed. 400 µl of washing liquid was added and stirred and the ferrite particles were attracted again by the same magnet and supernatant was removed. The processing was repeated 4 times. Then, 300 µl of same substrate solution used in IV was added and stirred. After 5 minutes at room temperature, luminance for 5 seconds was measured by the luminometer. The result is shown in Table 3.

TABLE 3

| | Assay of CA19-9 | | |
|---|---|---|---|
| Sample | Cartridge Well | Sample No. | Count Number (x10³) (counts/5 sec) |
| serum | 13 | 1 | 1.628 |
| | | 2 | 0.826 |
| | | 3 | 0.421 |
| | 15 | 4 | 0.126 |
| | | 5 | 0.543 |
| | | 6 | 0.968 |

IX—Preparation of HBs antigen sensitized ferrite particles

Ferrite particles available from Nippon Paint K.K. were dispersed in 800 µl at 5% concentration to which 2 ml of HBs antigen (400 µg/ml) was added, followed by stirring in an end-over-end mixer at room temperature for one night. The particles were washed 5 times with 2% BSA solution (0.1M Tris-HCl, 1 mM $MgCl_2$, pH 7.5) and dispersed in same BSA solution, resulting in HBs antigen sensitized ferrite particles.

X—Preparation of cartridge for particle type HTLV-I and HBs antibody detection

350 µl of HTLV-I antigen sensitized ferrite solution (0.008%/particle/BSA solution) prepared in III was poured to the well 4c of the cartridge 4 in FIG. 1e and 350 µl of HBs antigen sensitized ferrite solution (0.008%/particle/BSA solution) prepared in IX was added to the well 4d. Then 300 µl of anti human IgG mouse IgG sensitized alkaliphosphatase was poured to the well 4d. The cartridge was heat-sealed by an aluminum foil.

XI—Measurement of HTLV-I and HBs

The seal on the wells 4c, 4c', 4d and 4d' of the cartridge prepared in V were broken by the seal breaker and 20 µl of serum was added to the well 4d'. Further, 180 µl of diluent solution (0.1M Tris-HCl, 1 mM $MgCl_2$, 0.1 mM $ZnCl_2$, pH 7.0 containing 10% NRS, 2% BSA) was added thereto. Each 20 µl of this diluted serum was mixed with HTLV-I antigen sensitized particles in the well 4c and with HBs antigen sensitized particles in the well 4c'. After being stirred, these wells were put as they are at 37° C. for 10 minutes. Then, these wells were faced to a permanent magnet whose surface magnetic field is 3000 Gauss to attract the particles. Supernatant was removed by decantation and,then, 0.4% physiological salt solution was added and stirred. Ferrite particles were attracted by the same magnet and supernatant was removed in a similar manner. This processing were repeated by 2 times.

Each 250 µl of anti human IgG mouse IgG sensitized alkaliphosphatase solution (300 ng/ml protein solution) was added to the wells 4c and 4c' and put as they are for 10 minutes. The ferrite particles were attracted by the same magnet again and supernatant was removed by aspiration. 400 µl of 0.4% physiological salt solution was added and stirred and the ferrite particles were attracted again by the same magnet and supernatant was removed. The processing was repeated 4 times. Then, 300 µl of same AMPPD solution used in V-1 was added and stirred. After 5 minutes at room temperature, luminance for 5 seconds was measured by the luminometer. The result is shown in Table 4.

TABLE 4

Measurement of HTLV-I and HBs antibody

| Sample | | Count Number ($x10^3$) (counts/5 sec) | |
|---|---|---|---|
| | | Well 15 (HTLV-I) | Well 16(HBs) |
| only buffer | 1 | 0.006 | 0.002 |
| | 2 | 0.017 | 0.009 |
| | 3 | 0.006 | 0.012 |
| | 4 | 0.009 | 0.006 |
| | 5 | 0.015 | 0.007 |
| negative serum | 1 | 0.052 | 0.125 |
| | 2 | 0.072 | 0.132 |
| | 3 | 0.059 | 0.115 |
| | 4 | 0.078 | 0.131 |
| positive serum | 1 | 0.726 | 0.926 |
| | 2 | 0.718 | 12.821 |
| | 3 | 1.526 | 8.643 |

The cartridges prepared suitably as described are used in the apparatus. Now, the apparatus will be described in detail with reference to FIGS. 3 to 17.

Cartridge Stocker

Figure 3:
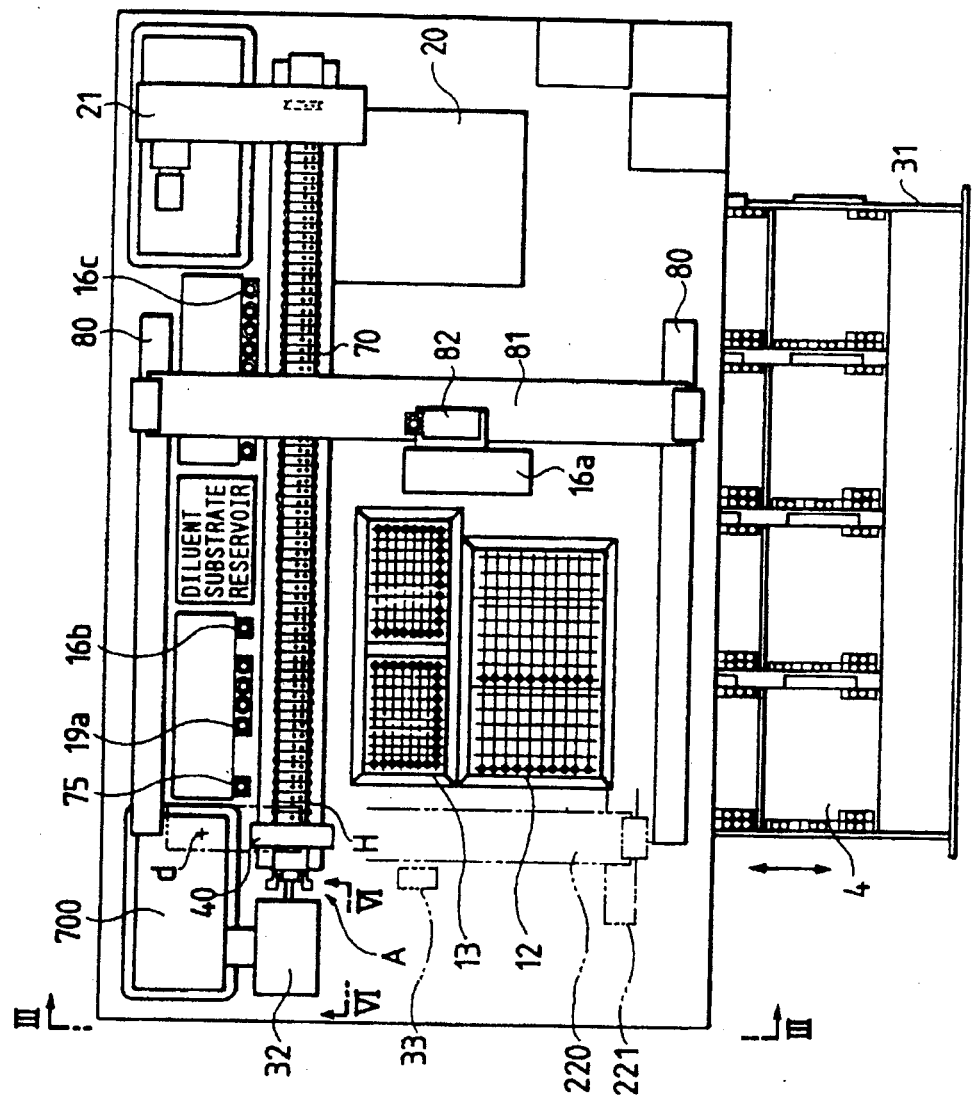

The cartridge stocker 31 stocking a plurality of the cartridges 4 in row and column matrix is removably inserted horizontally into the lower level portion of the apparatus shown in FIG. 3.

CARTRIDGE TRANSPORTATION MECHANISM

Figure 4:
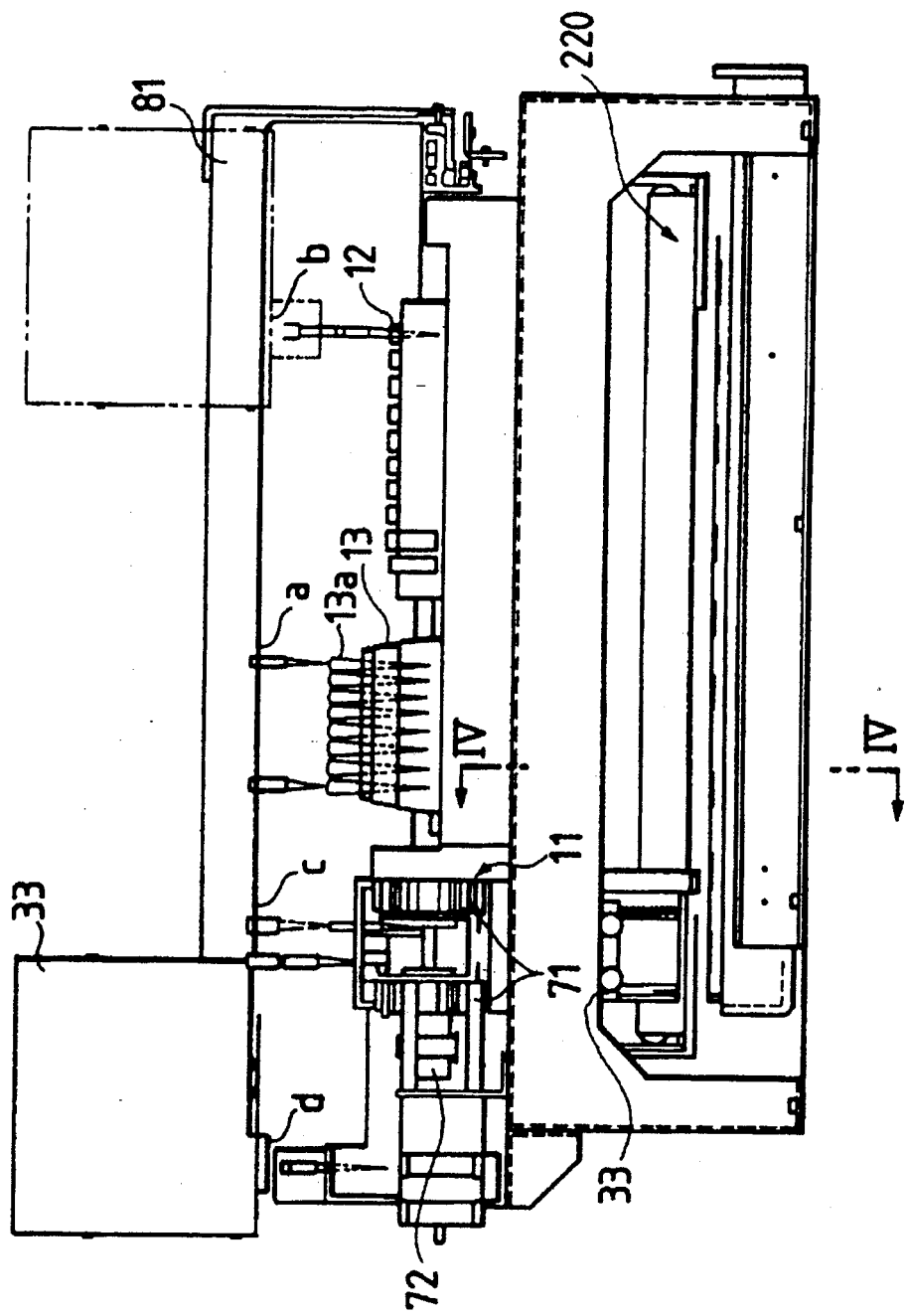

As shown in FIGS. 3 and 4, a cartridge transportation mechanism is arranged over the cartridge stocker 31. The mechanism extends along an insertion direction of the cartridge stocker 31 and is composed of a pair of rails 221 arranged perpendicularly to the extending direction and a crane arm 220 movable along the rails 221. A cartridge pick-up device 33 is mounted on the arm 220 movably therealong.

A mechanism for moving the arm 220 along the rails 221 and moving the pick-up device 33 along the arm 220 can be realized in any known mechanism such as used in a X-Y plotter. In this embodiment, the mechanism is realized by using reversible motors (not shown), pulleys (not shown) and wires arranged in a known manner.

These reversible motors are controlled by a suitable control mechanism such that the pick-up device 33 is moved to a predetermined position (shown by A in FIG. 3) so that the cartridges 4 arranged in X-Y matrix on the cartridge stocker 31 can be shifted one by one to that position.

PICK-UP DEVICE

Figure 5A:
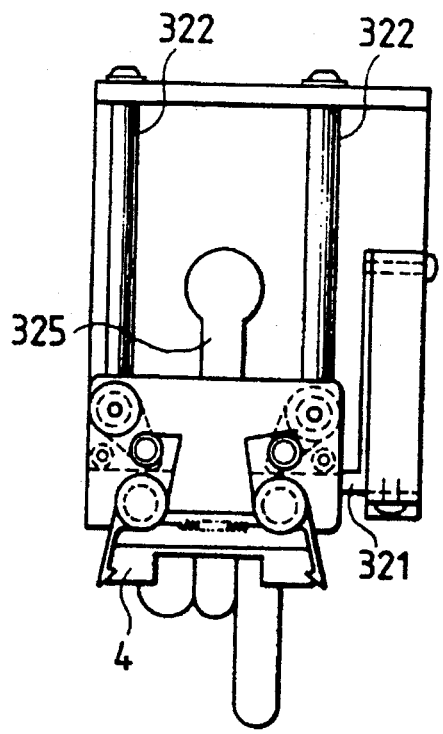
Figure 5B:
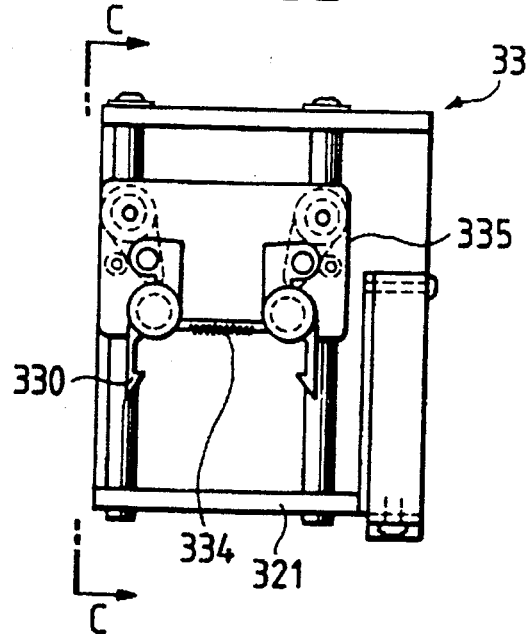
Figure 5C:
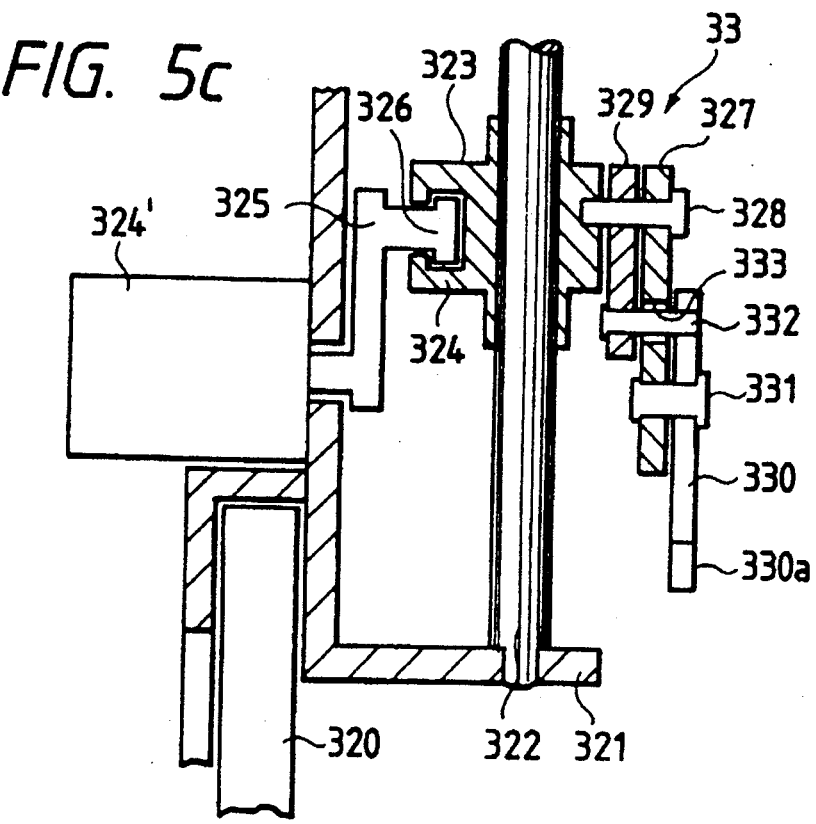

The pick-up device 33 is shown in FIGS. 5A to 5C in detail. The pick-up device 33 includes a vertically movable hook device. FIG. 5A is a front view of the hook device shown at an upper position. It is moved down to catch opposite ends of a cartridge 4 as shown in FIG. 5B. FIG. 5C is a side view of the pick-up device 33. In FIGS. 5A to 5C, the pick-up device 33 is moved to a position in which a selected cartridge 4 is disposed while holding the hook device in the state shown in FIG. 5B and when the pick-up device 33 reaches the certain cartridge 4 on the cartridge stocker 31, the hook device thereof is further lowered to catch the cartridge and then moved to the predetermined position A. At the position A, the pick-up device 33 is further lowered to put the cartridge 4 in the predetermined position A.

The pick-up device 33 includes a generally C shaped frame 321 slidably engaged with the arm 320 and a pair of vertical rods 322 provided in parallel between opposite end portions of the C shaped frame 321. A slider member 323 is slidably mounted on the rods 322. As shown in FIG. 5C, a lateral groove 324 is formed in a rear side surface of the slider member 323 and a motor 324' is fixedly mounted on the frame 321. An end of an arm 325 is fixedly connected to a shaft of the motor 324' and the other end of the arm 325 is formed with a protrusion 326 which is slidably fitted in the lateral groove. Thus, with rotation of the motor 324, the protrusion 326 of the arm 325 slides along the lateral groove 324, so that the slider member 323 is vertically driven.

A plate member 327 is fixedly secured to a front portion of the slider member 323 with a suitable gap therebetween. The gap is given by pins 328. A pair of cam levers 329 are arranged between the slider member 323 and the plate member 327 such that the levers 329 can be swung about the pins 328.

A pair of hook members 330 are mounted on the front surface of the plate member 327 rotatably about pins 331, respectively. Hooks 330a are formed in lower end portions of the hook members 330 and upper end portions thereof are rotatably connected with lower end portions of the cam levers 329 through a hole 333 formed in the plate member 327, such that they are rotatable about pins 332, respectively.

The hook members 330 are inwardly biased to each other by springs 334 as shown in FIG. 5A so that the right side cam lever 329, for example, is biased counterclockwise direction. In order to maintain the hook members 330 in the position shown in FIG. 5A, the clockwise movement of the cam levers 329 is limited by stoppers 335, respectively.

When the slider member 323 is lowered with rotation of the motor 324', the hook members 330 are lowered with the position shown in FIG. 5A. When the slider member 323 is lowered beyond a level in which the lower ends of the cam levers 329 contact with the lower edge of the frame 321, the lower end portions of the cam levers 329 are moved inwardly by the lower edge of the frame 321. Therefore, the hook members 330 are rotated away from each other to open the hooks 330a against the biasing force by the spring 334. Therefore, the cartridge 4 can be grasped thereby as shown in FIG. 5B. Then, when the slider member 323 is moved up, the cartridge 4 is lifted up by the hooks 330a stably with an aid of the spring 334.

The pick-up device 33 holding the cartridge 4 in 10 this manner is moved by the crane mechanism to the predetermined position A shown in FIG. 3 and then the pick-up device 33 is lowered again so that the cartridge 4 can be unhooked by a contact of the lower ends of the cam levers 329 with the lower edge of the frame 321. Thereafter, the pick-up device 33 is returned to a next position of the cartridge stocker 31.

LIFT MECHANISM

The lift mechanism 32 moves the cartridge 4 transported by the crane mechanism in the lower level up to an upper level and then onto a reaction line. Therefore, the lift mechanism 32 is arranged at the position A.

Figures 6A, 6B:
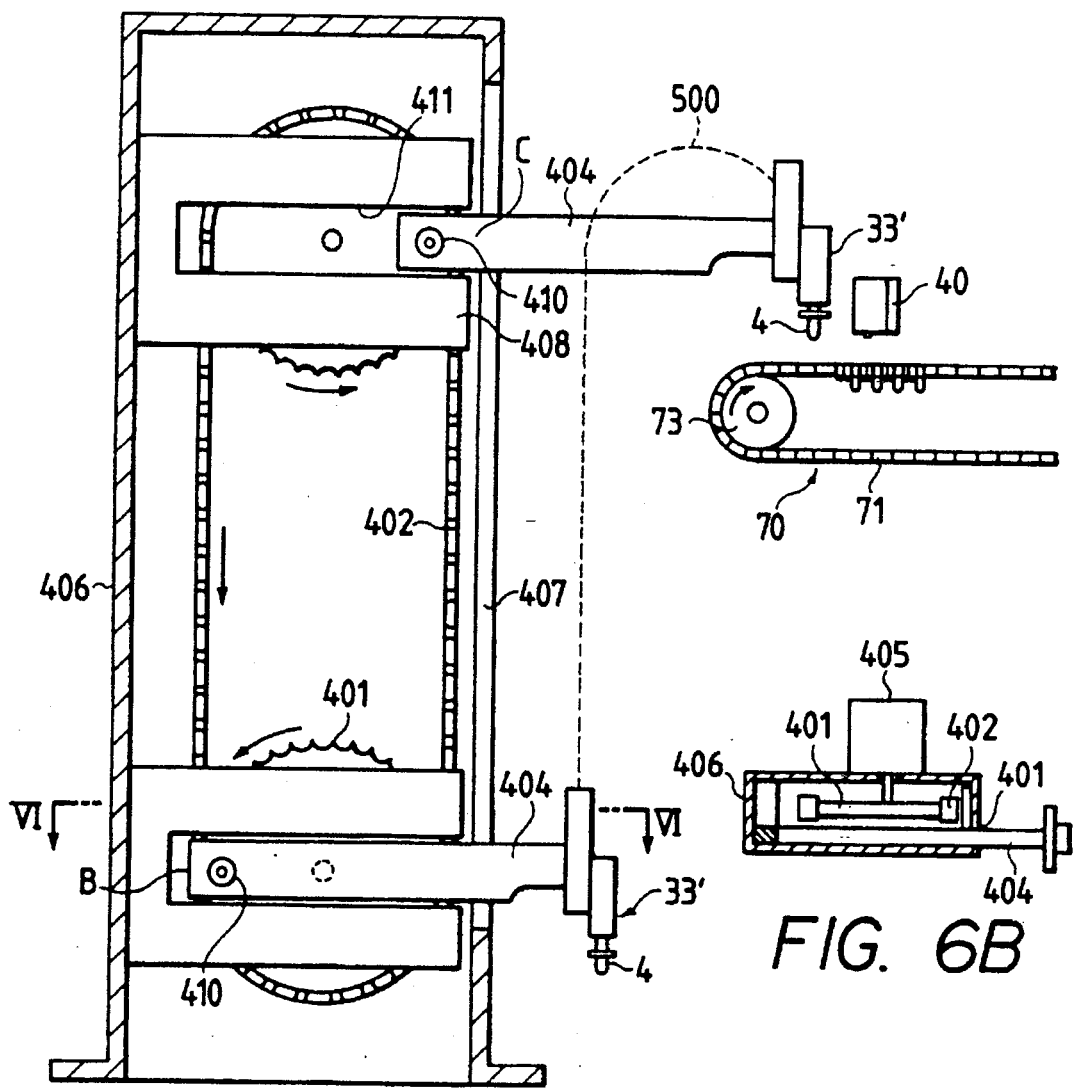

FIG. 6A and FIG. 6B which is a cross section taken along a line VI—VI in FIG. 6A show the lift mechanism 32. In FIGS. 6A and 6B, the lift mechanism 32 includes an upright frame 406 having a vertical slot 407 in its front wall, a reversible motor 405 (FIG. 6B) disposed outside the frame 406 and a pair of vertically arranged sprockets 401 fixedly disposed in the frame 406. Either one of the sprockets 401 is connected to a shaft of the reversible motor 405 so that a chain 402 can be driven reversibly on the sprockets 401 within a limited range as shown in FIG. 6A. A slider block 408 is housed in the frame 406 slidably vertically and has a lateral slot 411 opened to the front wall of the frame 406. An arm 404 is slidably received in the lateral slot 411. A rear end portion of the lateral arm 404 is rotatably connected to a position 410 on the chain 402 such that, when the slider block 408 is in the lowest position in the frame 406, the arm 404 is fully retracted and, after it passes the highest position in the frame, the arm is fully retracted as shown in FIG. 6A. In detail, a front portion of the arm 404 extends over the frame 406 through the vertical slot 407 thereof and is equipped with a pick-up device 33' similar to the pick-up device 33 of the transportation mechanism. The reversible motor 405 drives the sprocket reversibly to reciprocate the chain 402 within a range defined between positions B and C of the connecting point 410 of the rear end of the lateral arm 404 and the chain 402 such that the front end of the arm 404 moves along a locus shown by a dotted line 500 in FIG. 6A. That is, in FIG. 6A, the fully retracted arm 404 is moved by rotation of the sprocket 401 in the arrow direction up to the position of the upper sprocket 401. Then, after passing along an upper quarter circle of the upper sprocket 401, the lateral arm 404 is moved down while being protruded gradually and, finally, it is fully extended at the end of a subsequent quarter circle movement of the sprocket.

The semi-circle locus of the upper ends portion of the movement of the front end of the lateral arm 404 and hence the pick-up device 33' is important for the stable shift of the cartridge onto the reaction line 11.

The catching and releasing operation of the pick-up device 33' with respect to the cartridge 4 is the same as that mentioned with respect to FIGS. 5A and 5B. That is, at the lower position of the arm 404, the slide member is lowered to catch the cartridge and then moved up. Then, the device 33' is moved together with the arm 404 along the dotted locus 500 and, at the end of the locus 500, the slider member is lowered again to release the cartridge onto the reaction line 11.

II CONSTRUCTION OF UPPER LEVEL SAMPLER PORTION

As shown in FIG. 3, a sampling chip cassette 12 and a sample cassette 13 are arranged in a second, upper level. The sampling chip cassette 12 includes a plurality of sampling chips 44 arranged in a horizontal plane and the sample cassette 13 includes a plurality of sample containers. 13a, each containing a sample liquid containing substance to be measured, arranged in a plane.

REACTION LINE 11

Figure 2:
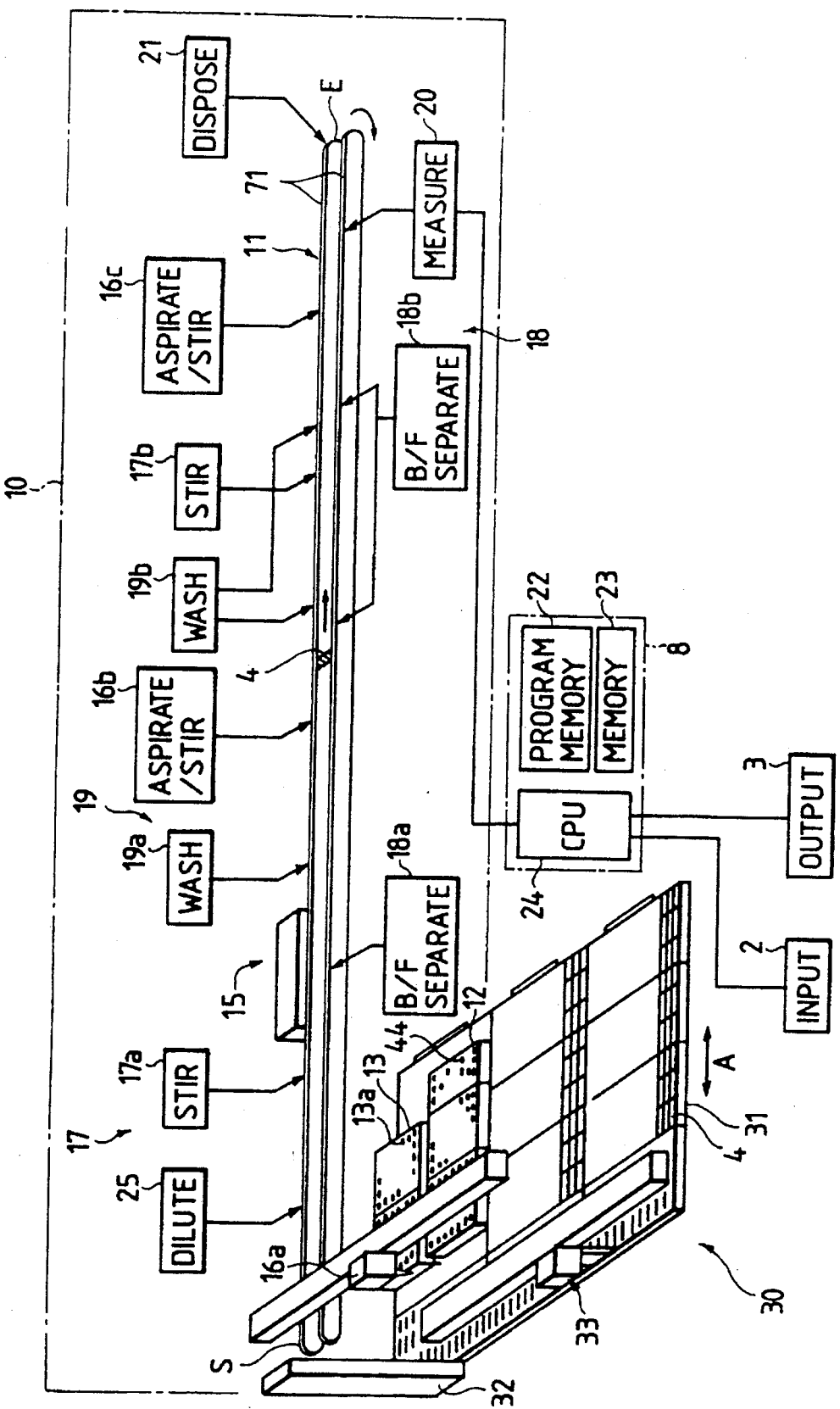

The reaction line 11 extends generally in a direction perpendicular to the inserting direction of the cartridge stocker 31 in the lower level. The reaction line 11 is composed of a pair of parallel endless belts 71 as shown in FIG. 2 and 3. The endless belts 71 support the opposite end portions of each cartridge 4, respectively, so that the cartridge can be stably moved therealong. The endless belts 71 are driven by sprockets 72 arranged in opposite end portions of the reaction line 11, which are in turn driven by stepping motors, such that the cartridge put on the reaction line can be stepped with an interval of, for example, 30 seconds.

The cartridge 4 lifted up by the lift mechanism 32 and put on a starting portion of the reaction line 11 is stepped to a next position on the reaction line 11 after 30 seconds and this is repeated until a measurement therefor completed. There are several devices arranged along the reaction line 11, which are necessary to provide a required reaction. Such devices will be described in detail later.

SEAL BREAKER

As mentioned previously, the cartridge 4 put on the starting point on the reaction line 11 has the wells sealed by the sealing film 11f. In order to remove such seal, a seal breaker 40 is provided above the reaction line 11 at a position next to the starting position. In the shown embodiment, the seal breaker takes the form of a block having a lower surface formed with a plurality (in this case, three) of downward protrusions so that, by lowering the block, portions of the sealing film 10f on the respective wells of the cartridge are broken by the protrusions to make the wells accessible. Since the design of such block is arbitrary and those skilled in the art can design it easily, the details thereof are not shown here.

SAMPLE CRANE MECHANISM

As shown in FIGS. 2 to 4, a sample transportation mechanism is provided above the upper level, which has substantially the same construction as that of the cartridge transportation mechanism except that a sampling pump unit 82 is mounted on an arm 81 instead of the pick-up device 33. In detail, the sampling crane mechanism includes a pair of rails 80, the arm 81 slidable along the rails 80 and the sampling unit 82 mounted on the arm 81 movably therealong. The movement of the pump unit 82 in a plane is substantially the same as that of the pick-up device 33.

SAMPLING PUMP UNIT

Figure 7:
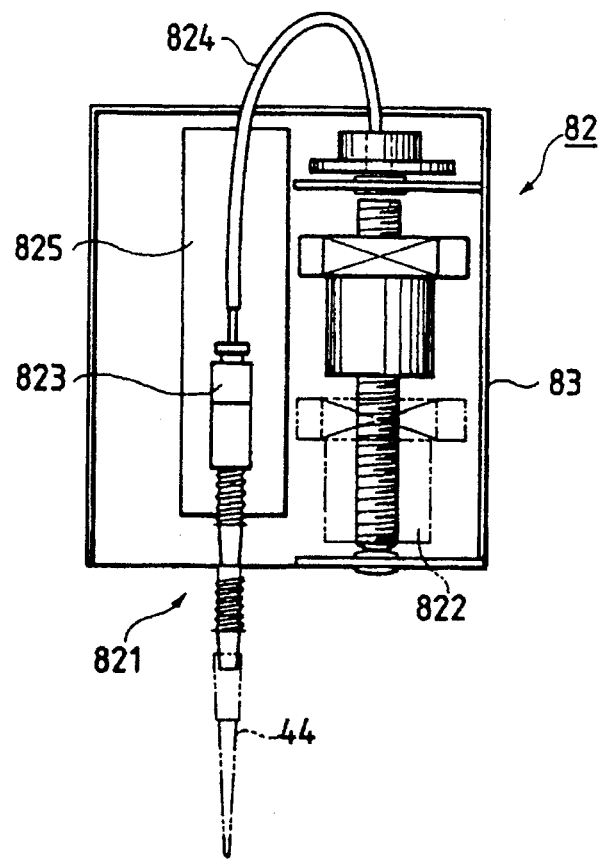

The sampling unit 82 shown in FIG. 7 includes a nozzle portion 821 and a pump portion 822 both arranged within a case 83 and connected to each other by a suitable tube 824. The nozzle portion 821 includes a nozzle 823 which is fixedly secured to a plate 825 which is movable vertically by means of a solenoid, for example. When the nozzle 823 is lowered, a top end thereof engages a chip 44 in the sampling chip cassette 12. Then, it is lifted up and moved to bring the chip 44 to a suitable location at which the pump portion 822 is actuated to aspirate a liquid contained therein and then moved another location to pour it thereto. Thereafter, moved it is to a location d (FIG. 3) to dispose the used chip into the chip disposer 700.

STIRRING PORTION AND B/F SEPARATOR

Figure 8:
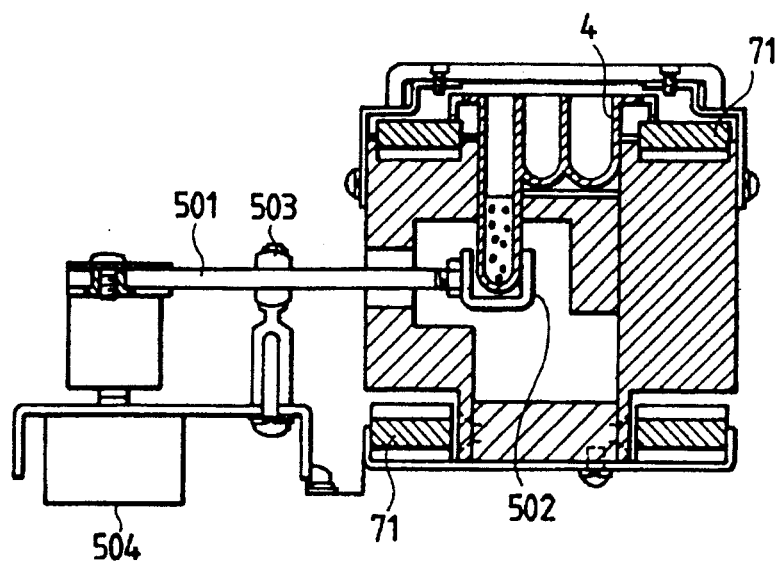
Figure 9:
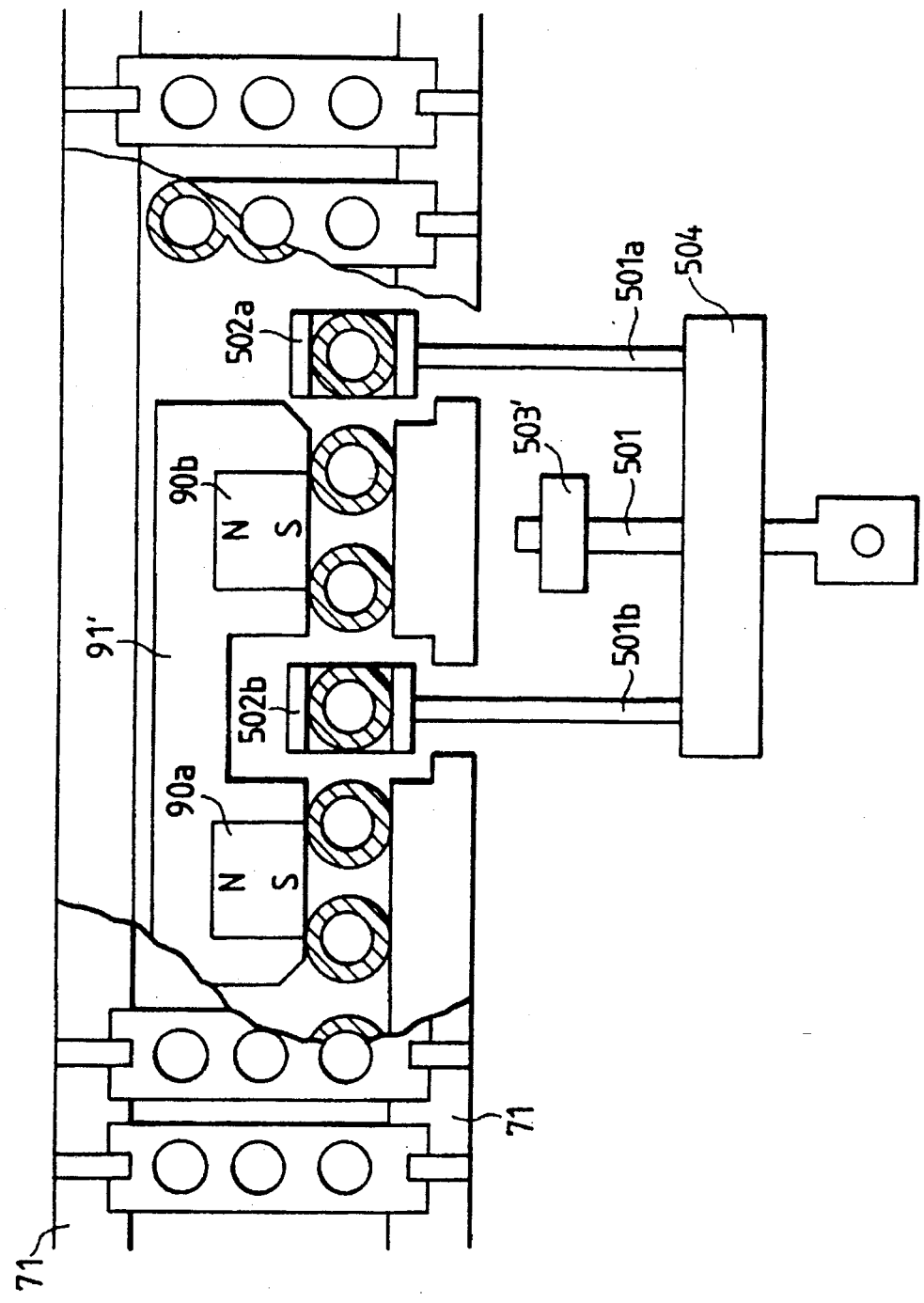

FIGS. 8 and 9 show an example of the stirring portion. In FIG. 8, which is a cross section of the stirring portion, a bar 501 has one end connected eccentrically to a shaft of a motor 504 and the other end mounting a U shaped member 502. A middle portion of the bar 501 is elastically supported by a support 503. The U shaped member 502 is adapted to fittingly receive the first well of the cartridge 4 transported by the endless belts 71. Upon rotation of the motor 504, the bar 501 is vibratingly driven thereby to vibrate the U shaped member 502 so that the first well received therein is vibrated to stir the content thereof. In FIG. 9 which is a plan view of a modification of the stirring portion shown in FIG. 8, a lateral beam 504 is fixedly secured to a middle portion of a bar 501 having one end eccentrically connected to a motor shaft and the other end elastically supported by a support member 503'. From opposite end portions of the lateral beam 504 a pair of bars 501a and 501b extend. Ends of the bars 501a and 501b mount U shaped members 502a and 502b, respectively. Between the U shaped members, a magnetic B/F separator 90 (FIG. 10) is disposed.

Figure 10:
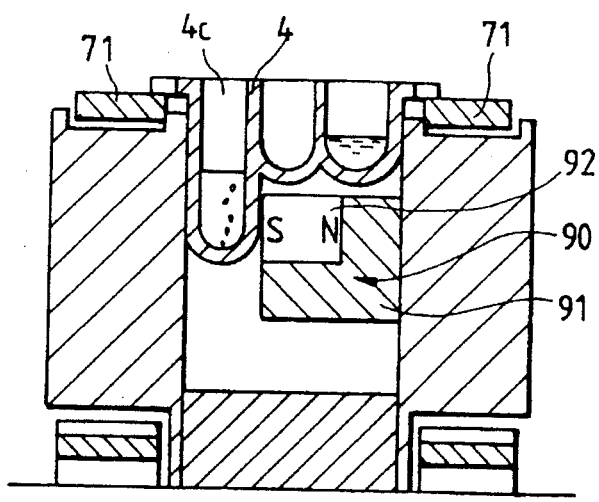

The B/F separator 90 includes a permanent magnet 92 supported by a magnetic member 91 arranged in one side of a passage of the first well of the cartridge 4 as shown in FIG. 10. By passing the magnet 92, magnetic particles contained therein are attracted to the wall of the cartridge well and, by washing the well with suitable washing liquid, free antigen or antibody can be removed.

Figure 11:
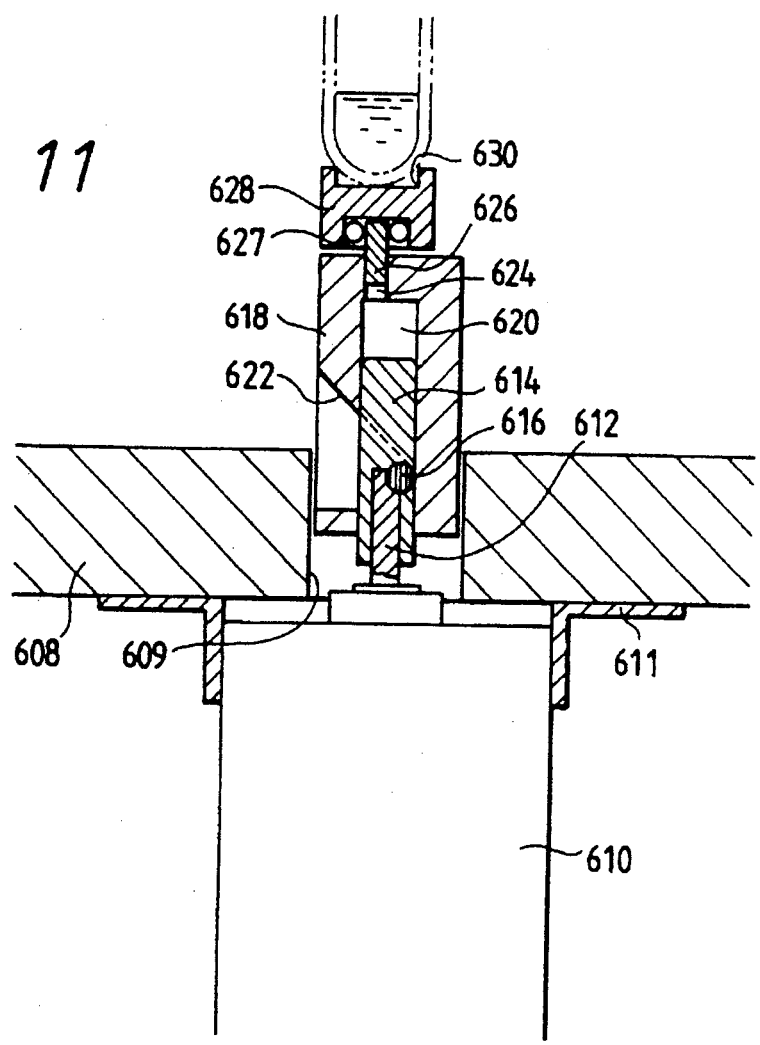

FIG. 11 shows another example of the stirring portion. In this example, a generally cylindrical member 618 of material whose specific weight is relatively large has a blind hole 620 and a cam slope 622 is formed in a wall of the cylinder by cutting. A plug member 614 is inserted into the blind hole 620. The plug member 614 has a blind hole into which a shaft of an upright motor 610 is fixedly inserted. The plug 614 has a protrusion 616 which follows the cam slope. In the bottom of the blind hole 620 of the cylinder 618, an eccentric hole 624 is formed into which a pin 626 is fixedly inserted. A well receiver member 628 is rotatably supported by an exposed portion of the pin 626 through a bearing 627. The well receiver member 628 has a recess 630 thereon on in which the well is received. Due to the weight, the cylinder member 618 tends to go down by gravity. Therefore, when out of operation, it is fully lowered such that the protrusion 616 of the plug 614 contacts with the uppermost position on the cam slope 622. When the motor 610 rotates counterclockwise direction, the plug 614 is rotated counterclockwise direction, so that the pin 616 thereof pushes the cylinder 618 up along the cam slope 622. When the cylinder 618 reaches the uppermost position at which the well receiver 628 receives the well, the cylinder 618 rotates is counterclockwise direction while keeping the positional relation to the well as it is. Since the well receiver 628 is slightly eccentric with respect to the cylinder 618, the receiver 628 is vibratingly rotated, so that the content of the well is stirred.

Figure 12:
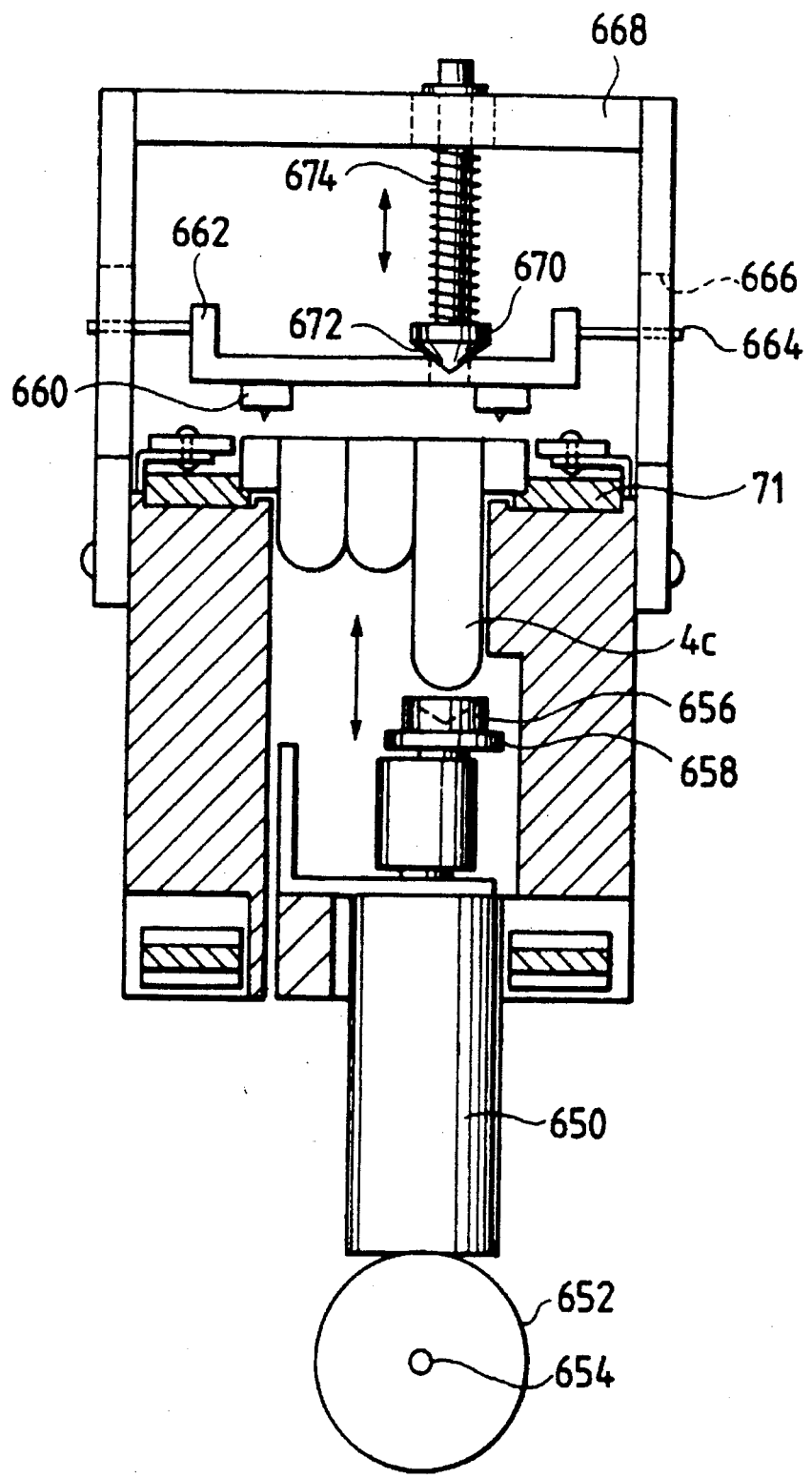

FIG. 12 shows another example of the stirring portion. In FIG. 12, an upright motor 650 is arranged between the endless belts 71 in such a manner that it can be moved vertically by, for example, a cam member 652 mounted on a lateral shaft 654 and in contact with a bottom of the motor 650. On a shaft of the motor, a well receiver 656 is eccentrically mounted rotatably through a bearing 658. In the upper position of the motor, the well receiver can receive a bottom portion of the cartridge well 4c carried by the belts 71 and, upon a further upward movement of the motor, the well receiver pushes the cartridge up.

When the cartridge is substantially pushed up, it abuts cartridge guides 660 formed on a lower surface of a holder member 662 at positions corresponding to the notches of the cartridge. A vertically movable range of the holder member is limited by engagements of lateral pins 664 thereof with vertical slots 666 formed in a generally reversed-U shape frame 668. Between the holder and the top portion of the frame, a fulcrum member 670 is provided, which has a pointed lower end which is received in a hole or recess 672 formed in the upper surface of the holder member. The fulcrum member is biased downwardly by a spring 674 to thereby bias the holder member down.

When the motor is moved up to the uppermost position by the cam member, it is energized to eccentrically rotate the well receiver to thereby stir the content of the well. In this case, since the holder member holds the upper portion of the cartridge stationarily, the eccentric vibrating movement of the well receiver can be efficiently transmitted to the well, resulting in sufficient stirring.

When a plurality of such stirring portions are arranged along the reaction line, the vertical movements of motors 650 thereof may be controlled by identical cam members to that (652) mounted on the same shaft at different angles, respectively.

MEASURING PORTION

Figure 13:
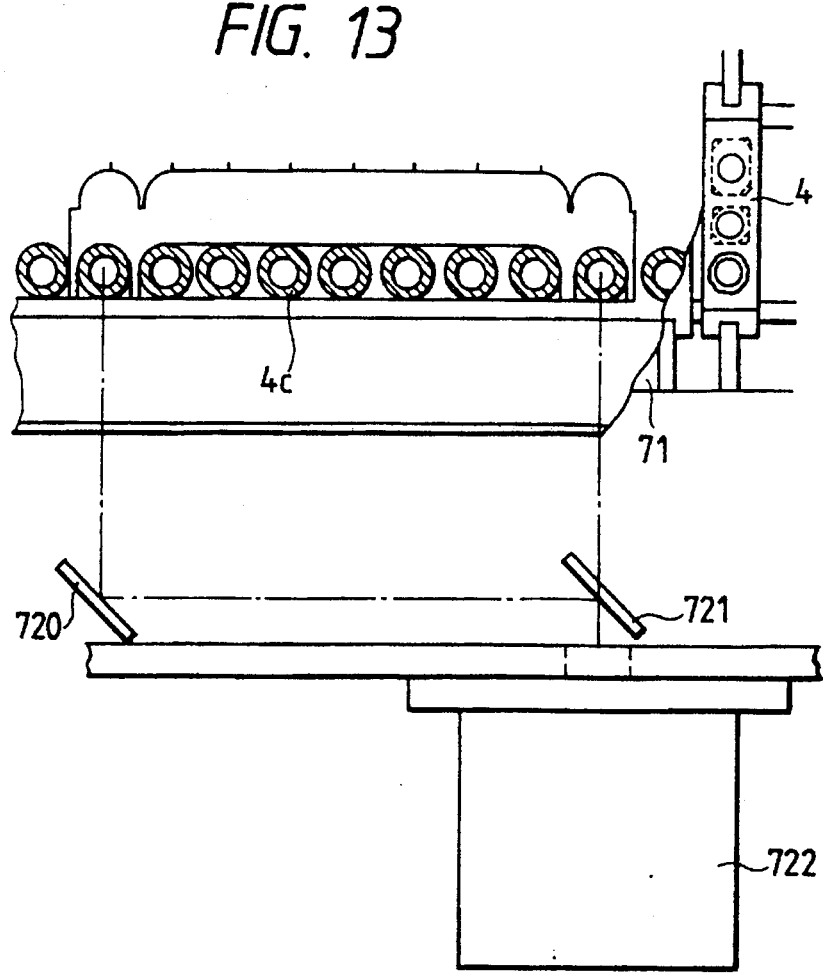

FIG. 13 shows an example of the measuring portion 20. This is to measure luminance of enzyme bound with magnetic particle carrying antigen or antibody at a specific wavelength. It includes a reflection mirror 720, a partial reflection mirror 721 and a photomultiplier 722. In this example, luminance at a time is measured by the photomultiplier 722 through the reflection mirror 720 and the partial reflection mirror 721 and luminance at a later time is measured through the partial reflection mirror 721 directly. A revolver may be associated therewith to remove error due to abnormal reflection light, if necessary.

Figure 14:
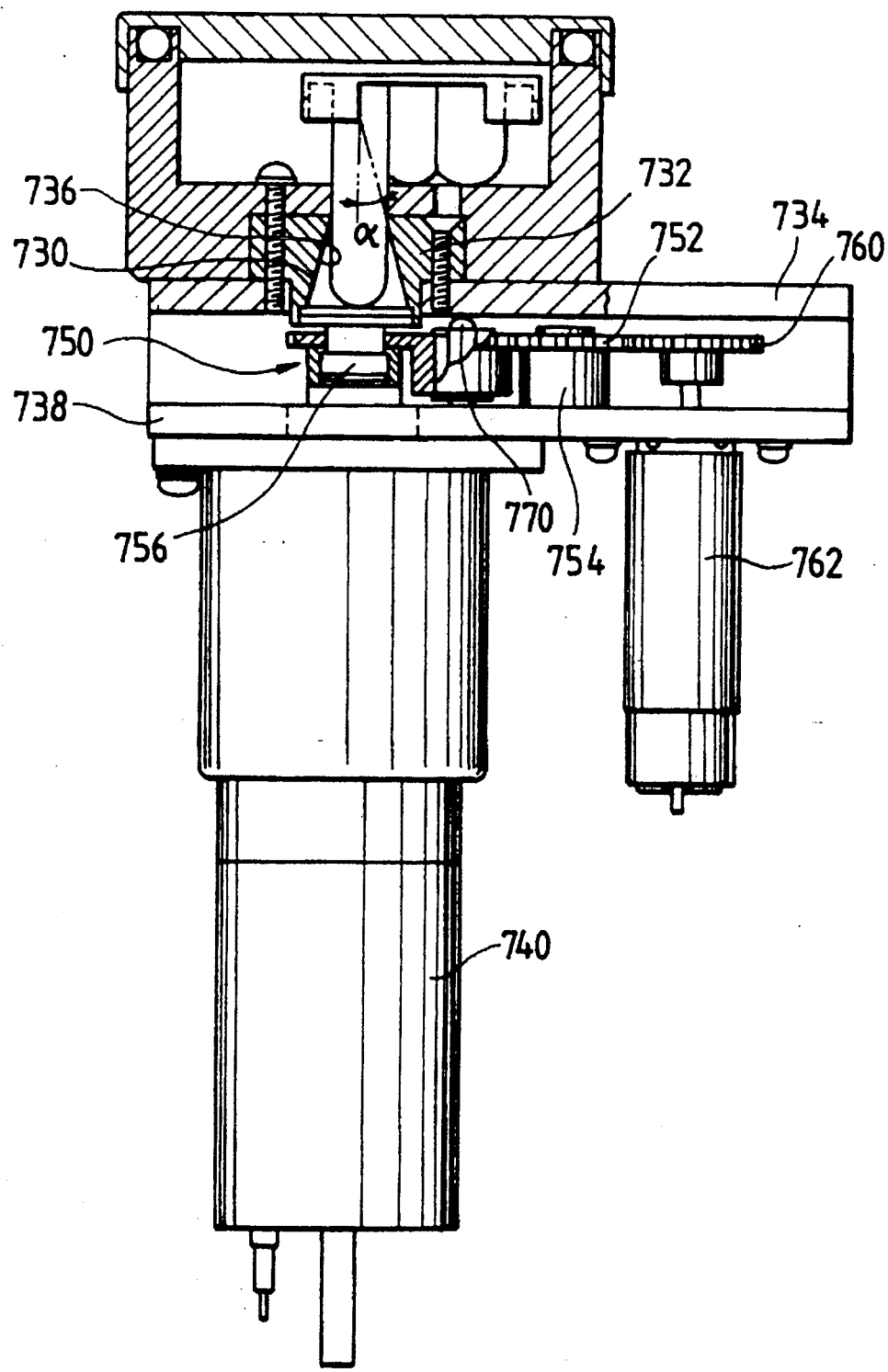

FIG. 14 shows another example of the measuring portion. In FIG. 14, the first well 4c of the cartridge 4 in which the desired reaction is to be measured is received in an upper opening of an optical reflective cylinder 730 in the form of a downwardly diverging hole formed in a block member 732 provided on a hole formed in a first deck 734, with an upper diameter thereof being substantially the same as that of the well 4c. An angle α of a taper wall 736 of the cylinder 730 may be within a range from 10° to 60°. However, it has been found that a satisfactory result is obtained when the angle sis about 30°.

A second deck 738 is provided below the deck 734 in parallel to each other. The second deck 738 has a hole corresponding, in position and size, to the hole of the first deck 734. A photo multiplier 740 is arranged correspondingly to the cylinder 730 below the hole of the second deck 738 by a suitable means.

A filter 750 is disposed between the first deck and the second deck. The filter 750 includes a disc 752 rotatably supported by a pin 754 supported between the decks. The disc 752 has a plurality of holes formed along a peripheral portion thereof in each of the holes a filter member 756 is disposed.

Figure 15:
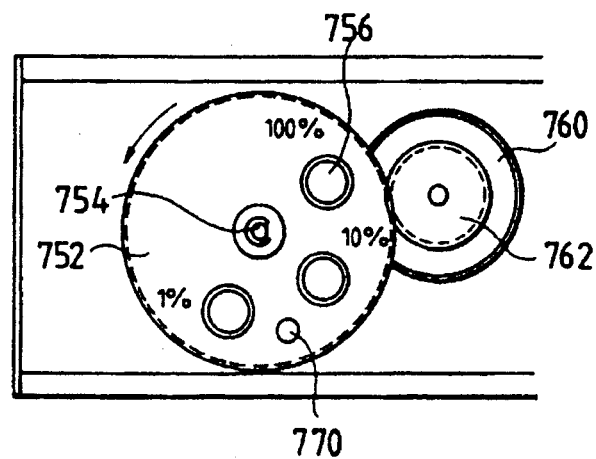

The peripheral edge of the disc is geared to mesh with a gear 760 mounted on a shaft of a motor 762 so that the disc 752 is rotated by the motor 762 to put a desired filter member 756 exactly in the position between the cylinder 730 and the photo multiplier 740. FIG. 15 shows the relative positions of the disc 752, the motor 762 and the gear 760.

Three filter members 756 are provided in the shown embodiment, which have transparencies of 1%, 10% and 100%, respectively. The number of the filter members and their transparencies can be selected arbitrarily on demand.

A position sensor 770 is provided on the disc 752 to detect a rotational angle of the disc. The sensor 770 may be a magnetic sensor. According to an output of the sensor 770, the motor 762 is controlled to position a desired filter member in place.

Figure 16:
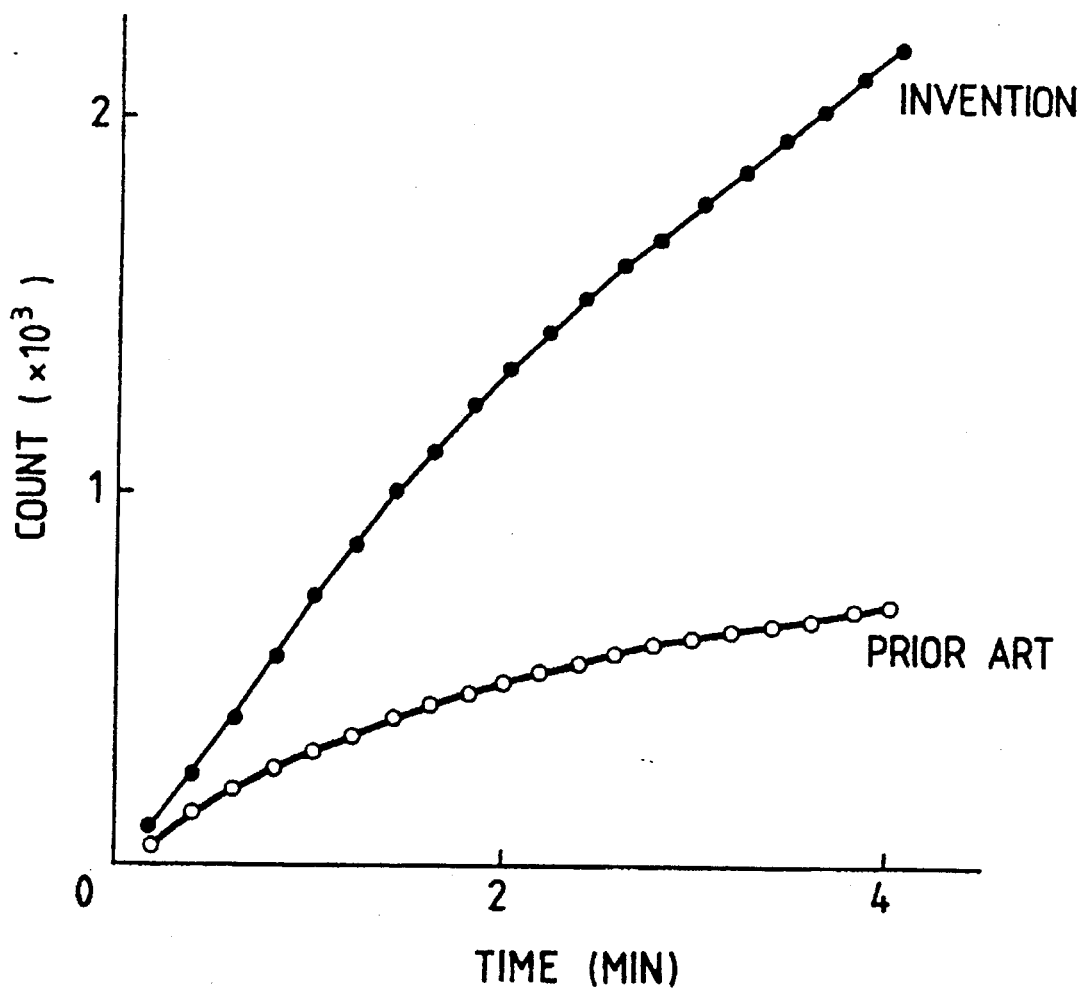

The taper wall 736 of the cylinder 730 is important as mentioned previously. FIG. 16 shows the result of an experiment conducted to clarify the effect of the taper cylinder. In this experiment, luminance of a mixture of 0.1M tris buffer solution (pH9.8), 20 µl of alkaliphosphatase (1 µg/ml) and 300 µl of AMPPD is measured with and without the cylinder 730 having a taper angle of 30°.

CARTRIDGE DISPOSER

Figure 17:
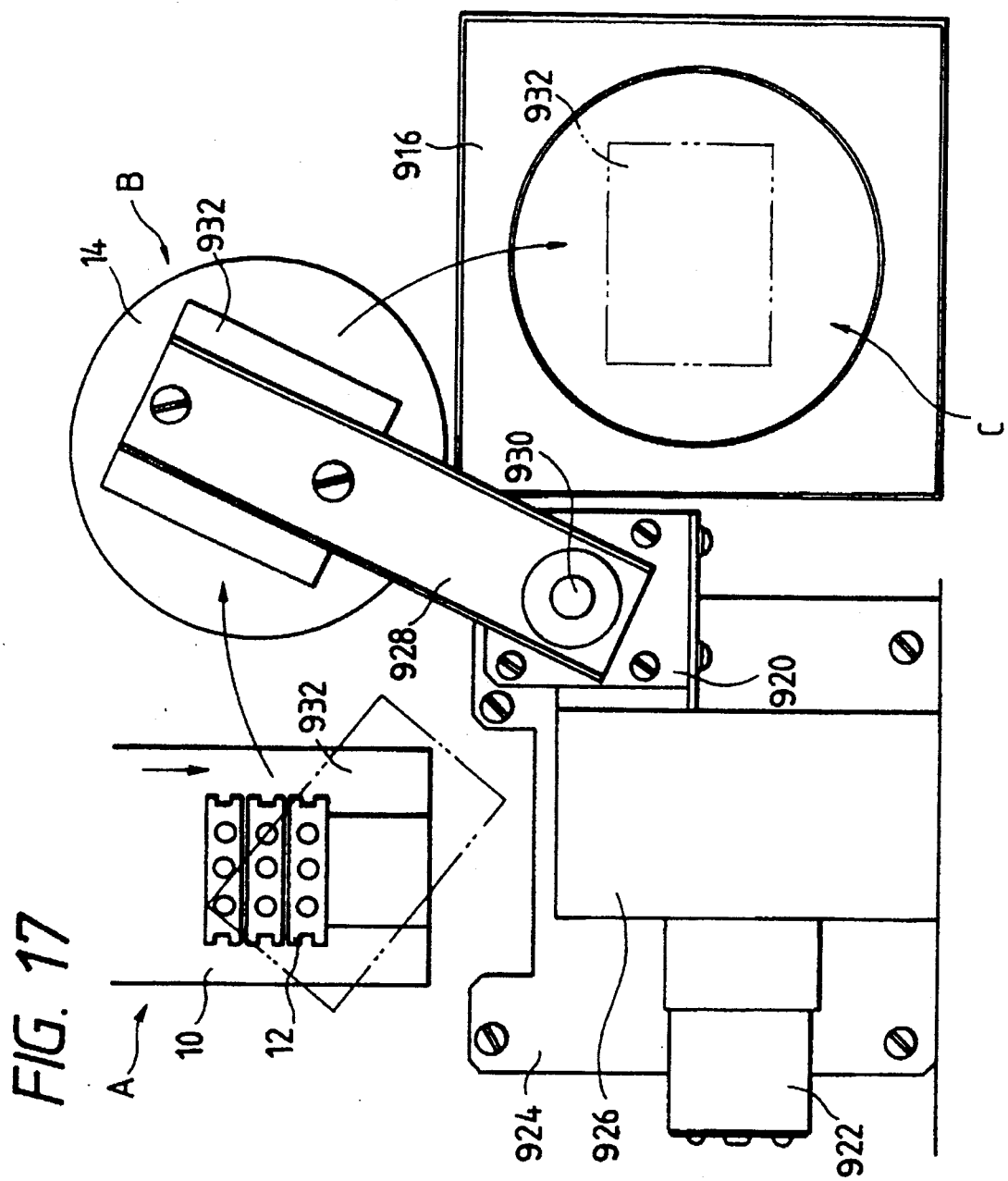
Figure 18:
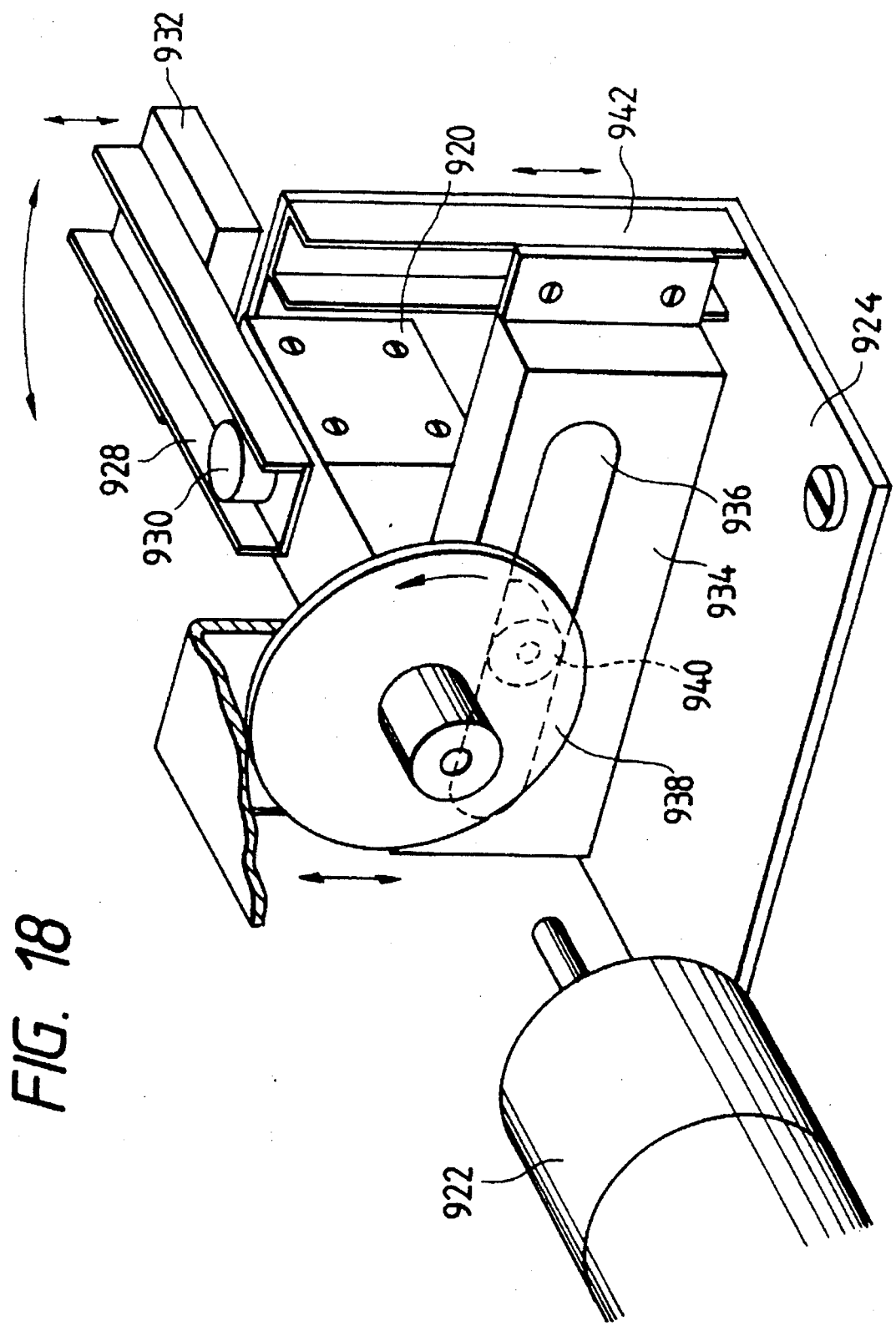

FIG. 17 is a plan view of the cartridge disposer and FIG. 18 is a perspective view of the cartridge disposer 21 shown in FIG. 2. In FIGS. 17 and 18, the cartridge disposer 21 is disposed at an end portion of the reaction line 11 at which the cartridges 4, the measurements of which are completed, arrive one by one. The disposer includes an arm elevation device 926 mounted on a base 924. The elevator device includes a pair of vertical rails 942, a cam block 934 supported vertically slidably by the rails, a d.c. motor 922 having a shaft supporting a disc 938 provided on its periphery with a roller 940 which engages with a cam slot 936 formed horizontally in the cam block 934, a block 920 fixedly secured to the cam block 934 and housing a stepping motor, an arm 928 having one end fixedly connected to a shaft of the stepping motor and a pick-up device 932 mounted on the other end of the arm 928.

The pick-up device 932 may have substantially the same construction as that of the pick-up device 33 of the cartridge crane mechanism, with some parts being removed.

In operation, the cam block 934 is lifted along the rails 942 by a rotation of the motor 922 through the disc 938, the engagement of the roller 940 thereof with the cam slot 936. Then, the stepping motor of the block 920 is actuated when a cartridge arrives at the end of the reaction line to bring the other end of the arm 928 and hence the pick-up device 932 above the arrived cartridge. Thereafter, the cam block 934 is lowered onto the cartridge so that the pick-up device 932 can engage the cartridge in the same manner as mentioned with respect to the pick-up device 33 of the cartridge transportation mechanism. Then, the cam block is lifted again and the arm 928 is rotated in reverse direction above the disposer container 916. At this position, the pick-up device 932 is actuated to release the cartridge to allow it to drop into the container. This sequence of operations is repeated for each cartridge arriving.

FIGS. 19 to 22 show flowcharts of the one-step method, the two-step method, the delay method and the two-step method with dilution, to be performed by the present apparatus, respectively. In these flowcharts, the steps S1 and S2 are common for all of these methods. In step S1, an operator actuates the start button 2a of the input portion 2 so that the transportation of the cartridges in the cartridge stocker is started one by one to the start position on the reaction line through the cartridge crane mechanism and the cartridge lift mechanism and to break the seal of the cartridges on the reaction line successively through the seal breaker (step S2). Then the operator operates the selection button 2b thereof to select a program corresponding to a reaction to be obtained. The CPU 24 reads out the selected program from the program memory and starts to control the operation of the various portions of the apparatus so that the selected program can be performed.

Figure 19:
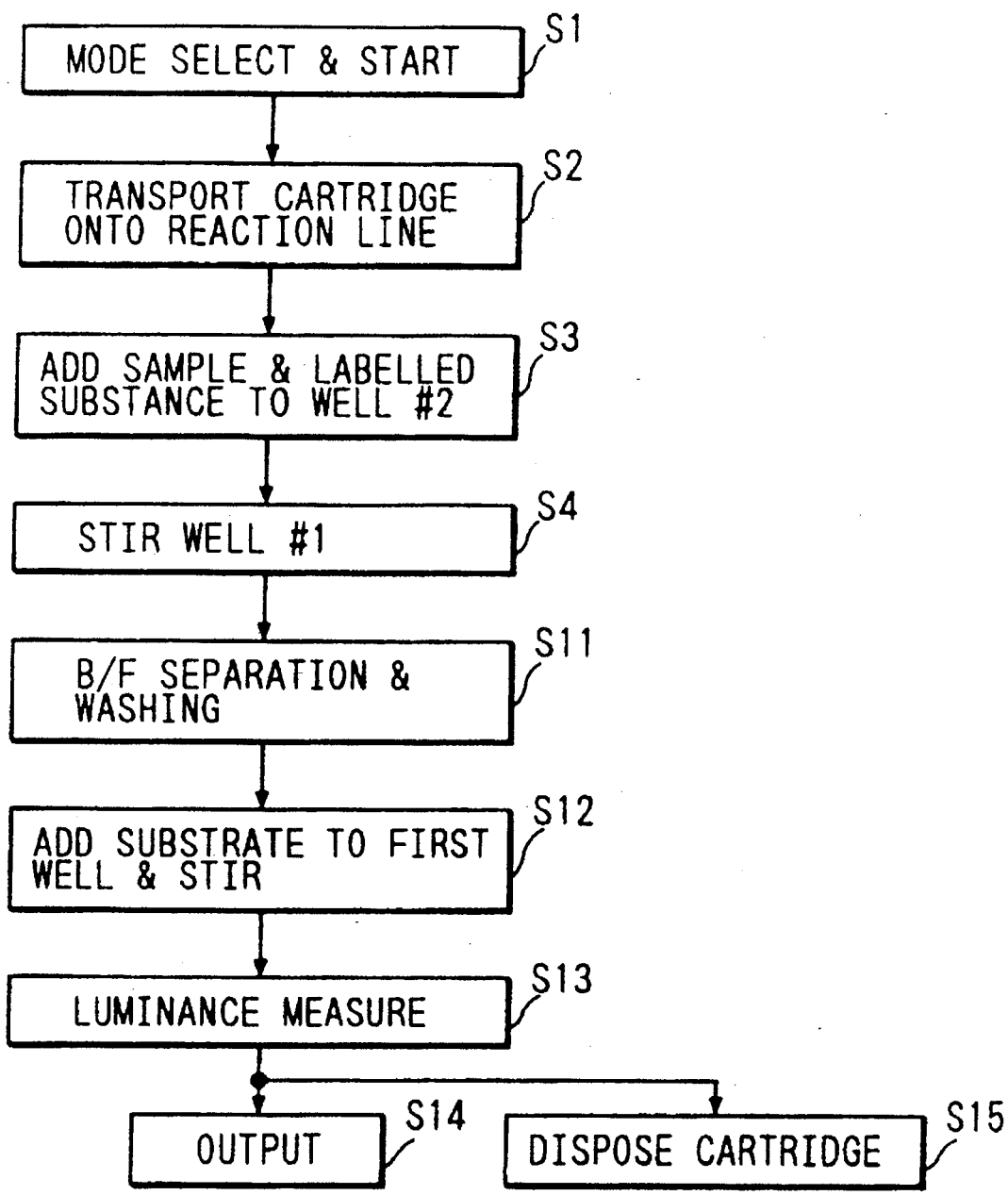

In FIG. 19 which shows the one step method mentioned above, the sampling crane mechanism and the aspirating/pouring portion are actuated to pick up a chip into which a sample is taken in by aspiration and poured into a first well of the cartridge, which contains magnetic particles carrying antigen or antibody, and, after the chip is disposed, to pick up another chip into which enzyme labelled substance contained in a second well of the cartridge is taken in and poured to the first well (step S3). Then, the first stirring portion 17a is activated to stir the mixture in the first well of the cartridge moved to a next position on the reaction line 70 (step S4). Then, when the cartridge reaches a first magnetic B/F separator 18a, a B/F separation is performed, followed by washing by means of a first washing portion 19a (Step S11). Then, substrate is added to the first well by the substrate pouring portion 16c and stirred in the second stirring portion 17b (Step S12). Then, an optical measurement is performed by the measuring portion 20 (Step S13) and an output thereof is supplied to the CPU 24 (Step S14). At the same time, the cartridge is disposed by the disposer portion (Step S15).

Figure 20:
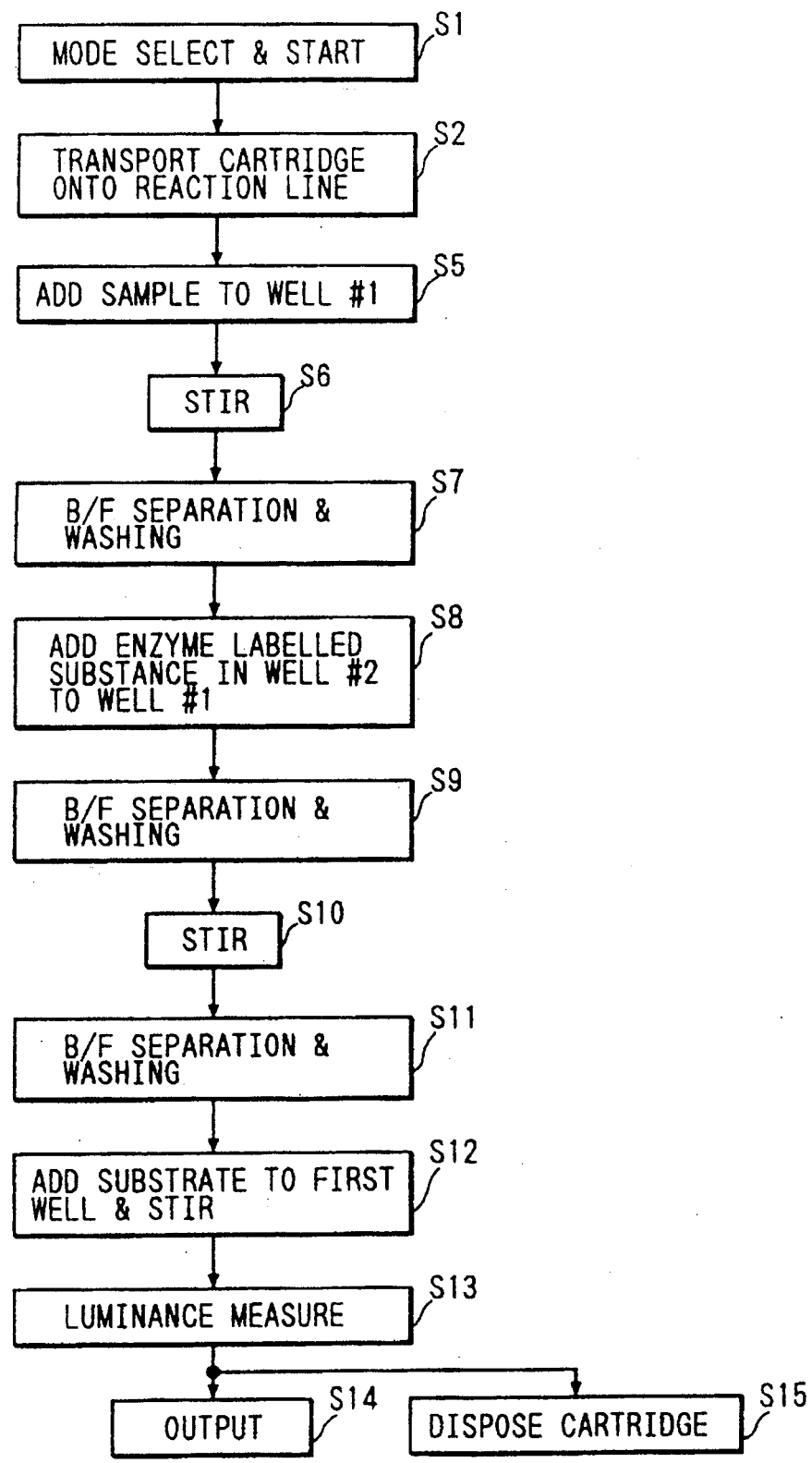

FIG. 20 shows the two step method mentioned above. After the step S2, a sample is poured to a first well of the cartridge, which contains magnetic particles carrying antigen or antibody (Step S5). Then, the first stirring portion 17a is activated to stir the mixture in the first well of the cartridge moved to a next position on the reaction line 70 (step S6). Then, when the cartridge reaches a first magnetic B/F separator 18a, a B/F separation is performed, followed by washing by means of a first washing portion 19a (Step S7). Then, enzyme labelled substance contained in a second well of the cartridge is poured to the first well and stirred (Step S8). Thereafter, a magnetic B/F separation and washing are performed in the Step S9. Then, after stirred again in the Step S10, substrate is added to the first well by the substrate pouring portion 16c and stirred in the second stirring portion 17b (Step S12). Then, an optical measurement is performed by the measuring portion 20 (Step S13) and an output thereof is supplied to the CPU 24 (Step S14). At the same time, the cartridge is disposed by the disposer portion (Step S15).

Figure 21:
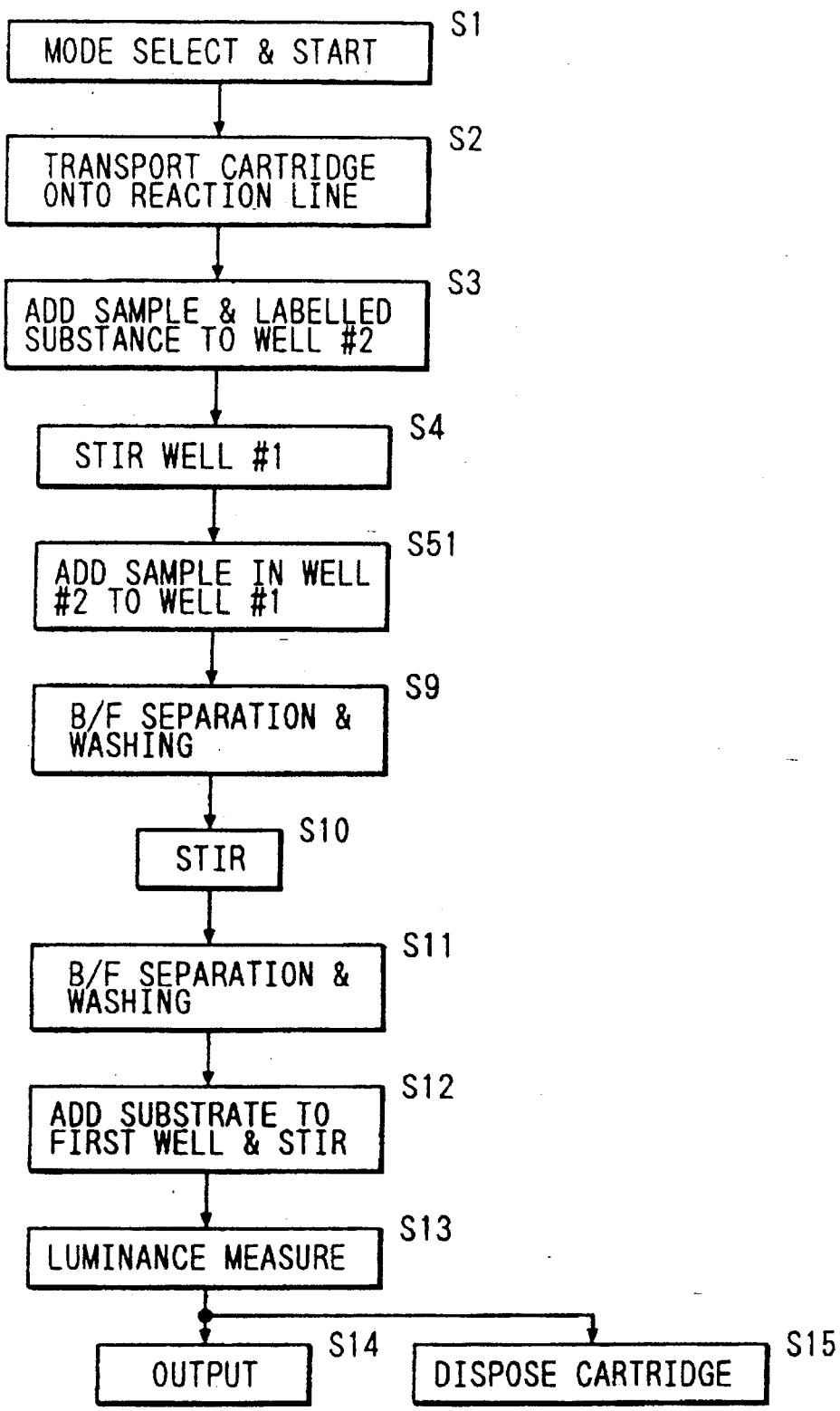

FIG. 21 shows the delay method using dilution mentioned above in which the steps S1 to S4 are the same as those in FIG. 18. After the step S4, magnetic particles carrying antigen or antibody contained in a first well of the cartridge are mixed with a sample and enzyme labelled substance and the mixture is stirred by the first stirring portion (Step S51). Then, the Steps S9 to S15 are performed with respect thereto as in the steps shown in FIG. 20.

Figure 22:
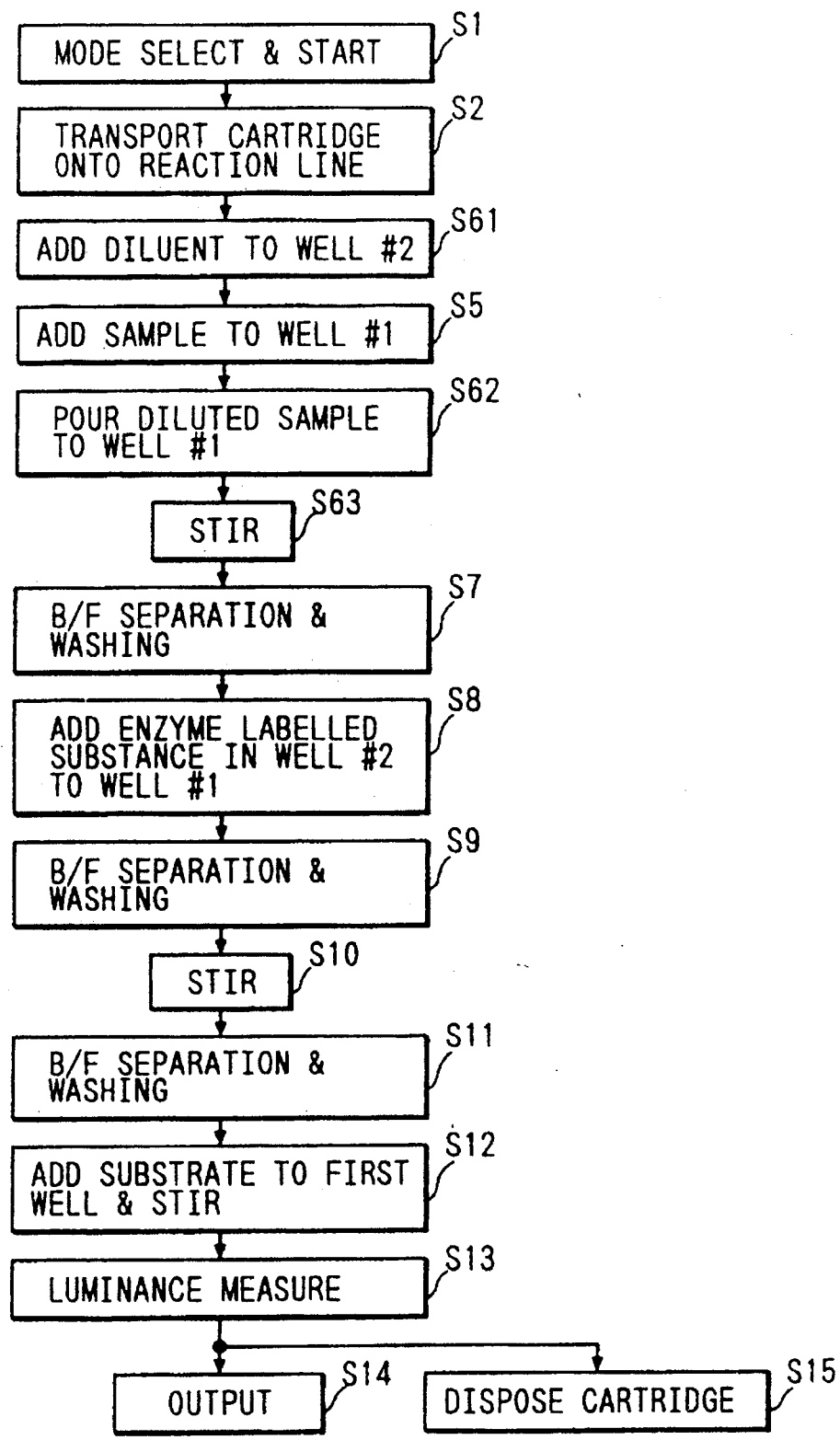

FIG. 22 shows the two step method using diluent. In FIG. 22, after the step S2, diluent is poured to a first well of the cartridge from the diluting portion 25 (Step S61) and a sample is poured to the same well (Step S5). The resultant diluted sample is poured to a second well containing magnetic particles carrying antigen or antibody (Step S62). Then, after being stirred by the first stirring portion 17a (Step S63), a B/F separation and washing are performed in Step S7. Thereafter, the same steps 8 to 15 are performed as in the two step method shown in FIG. 20.

As described hereinbefore, according to the present invention, a sequence of operations necessary to perform an immunoassay measurement can be completely automated by the use of the cartridges each having at least two wells, at least one of which contains solid phase material, and the reaction line for steppingly moving these cartidges one by one while performing necessary operations with respect to the cartridges by means of at least one B/F separator, at least one stirrer, at least one pouring portion, at least one washing portion, an optical measuring portion, etc., arranged along the reaction line in a suitable order. The cartridges described may be modified respectively to accommodate desired applications. The consitutional components of the present apparatus can be also modified suitably. Such modifications are fall in the scope of the present invention.

What is claimed is:

1. A cartridge for use in immunoassay, comprising a resin mold block having a rectangular flat portion formed at opposite ends with notches and a plurality of wells, at least a first one of said wells being deeper than the other wells and containing magnetic particles carrying antigen or antibody and at least one of the other wells being filled with labelled antigen or antibody solution.

2. The cartridge claimed in claim 1, wherein said wells comprise the first well, a second well being empty, and a third well containing antibody or antigen labelled with labelling compound.

3. The cartridge claimed in claim 1, wherein said labelled antigen or antibody is antigen or antibody labelled with an enzyme.

4. The cartridge claimed in claim 2, wherein said labelled antigen or antibody is antigen or antibody labelled with an enzyme.

5. The cartridge claimed in claim 1, wherein said cartridge is of optically transparent and non-magnetic material.

6. The cartridge claimed in claim 2, wherein said cartridge is of optically transparent and non-magnetic material.

* * * * *